US011127499B2

United States Patent
Ramanan

(10) Patent No.: US 11,127,499 B2
(45) Date of Patent: Sep. 21, 2021

(54) REAL-TIME DETECTION OF PERIODIC BREATHING

(71) Applicant: ResMed Pty Ltd, Bella Vista (AU)

(72) Inventor: Dinesh Ramanan, Sydney (AU)

(73) Assignee: ResMed Pty Ltd

( * ) Notice: Subject to any disclaimer, the term of this patent is extended or adjusted under 35 U.S.C. 154(b) by 856 days.

(21) Appl. No.: 15/117,040

(22) PCT Filed: Feb. 13, 2015

(86) PCT No.: PCT/AU2015/050055
§ 371 (c)(1),
(2) Date: Aug. 5, 2016

(87) PCT Pub. No.: WO2015/120521
PCT Pub. Date: Aug. 20, 2015

(65) Prior Publication Data
US 2017/0164906 A1    Jun. 15, 2017

(30) Foreign Application Priority Data

Feb. 13, 2014   (AU) .................................. 2014900435

(51) Int. Cl.
*G16H 40/63* (2018.01)
*A61B 5/087* (2006.01)
(Continued)

(52) U.S. Cl.
CPC ............. *G16H 40/63* (2018.01); *A61B 5/087* (2013.01); *A61B 5/0816* (2013.01);
(Continued)

(58) Field of Classification Search
None
See application file for complete search history.

(56) References Cited

U.S. PATENT DOCUMENTS

| 4,944,310 A | 7/1990 | Sullivan |
| 6,532,959 B1 | 3/2003 | Berthon-Jones |

(Continued)

FOREIGN PATENT DOCUMENTS

| JP | 2004526470 A | 9/2004 |
| WO | 2006066337 A1 | 6/2006 |

(Continued)

OTHER PUBLICATIONS

JP Office Action issued in corresponding JP application No. 2016-551719 dated Dec. 26, 2018.
(Continued)

*Primary Examiner* — Jacqueline Cheng
*Assistant Examiner* — Jairo H Portillo
(74) *Attorney, Agent, or Firm* — Botos Churchill IP Law LLP

(57) ABSTRACT

A method for a device detects periodic breathing in a patient. The method may include receiving a series of event intervals bounded by apnea or hypopnea events detected in respiration of the patient, and processing, upon closure of an event interval, the event interval to determine a character of the event interval, such as any of: probably a periodic breathing cycle; probably not a periodic breathing cycle; and uninformative. The method may further include determining whether to change a current periodic breathing state that indicates whether a periodic breathing episode is in progress, based on a history of event interval characters that is long compared to the typical length of a periodic breathing cycle real-time detection of periodic breathing.

28 Claims, 25 Drawing Sheets

(51) Int. Cl.
    *A61B 5/00* (2006.01)
    *A61B 5/08* (2006.01)
    *A61M 16/00* (2006.01)
    *A61M 16/10* (2006.01)

(52) U.S. Cl.
    CPC .......... *A61B 5/4818* (2013.01); *A61B 5/4836* (2013.01); *A61B 5/7282* (2013.01); *A61M 16/0051* (2013.01); *A61M 16/0057* (2013.01); *A61M 16/024* (2017.08); *A61M 16/107* (2014.02); *A61M 16/1055* (2013.01); *A61M 2016/0018* (2013.01); *A61M 2205/502* (2013.01); *A61M 2230/40* (2013.01)

(56) References Cited

U.S. PATENT DOCUMENTS

| | | | |
|---|---|---|---|
| 6,589,188 B1* | 7/2003 | Street | A61B 5/0205 |
| | | | 600/508 |
| 7,371,220 B1 | 5/2008 | Koh et al. | |
| 7,413,549 B1 | 8/2008 | Koh | |
| 2002/0088465 A1 | 7/2002 | Hill | |
| 2005/0241639 A1* | 11/2005 | Zilberg | A61B 5/0803 |
| | | | 128/204.21 |
| 2007/0239055 A1 | 10/2007 | Sowelam et al. | |
| 2008/0092894 A1 | 4/2008 | Nicolazzi et al. | |
| 2010/0100000 A1 | 4/2010 | Lee et al. | |
| 2010/0113957 A1* | 5/2010 | Williams | A61B 5/087 |
| | | | 600/538 |
| 2012/0029362 A1* | 2/2012 | Patangay | A61B 5/0205 |
| | | | 600/484 |
| 2012/0071741 A1 | 3/2012 | Moussavi et al. | |
| 2012/0088992 A1 | 4/2012 | Armitstead | |
| 2013/0333696 A1 | 12/2013 | Lee et al. | |
| 2014/0188006 A1* | 7/2014 | Alshaer | A61B 5/7282 |
| | | | 600/586 |
| 2015/0038867 A1 | 2/2015 | Armitstead et al. | |

FOREIGN PATENT DOCUMENTS

| | | |
|---|---|---|
| WO | 2013110136 A1 | 8/2013 |
| WO | 2013152403 A1 | 10/2013 |

OTHER PUBLICATIONS

International Search Report for Application No. PCT/AU2015/050055 dated May 28, 2015.
Extended European Search Report for Application No. EP15748505 dated Aug. 17, 2017.
NZ Examination Report dated Nov. 30, 2020 for New Zealand Patent Application No. 761422.

* cited by examiner

REAL-TIME DETECTION OF PERIODIC BREATHING

1 CROSS-REFERENCE TO RELATED APPLICATIONS

The present application is a national phase entry under 35 U.S.C. § 371 of International Application No. PCT/AU2015/050055 filed Feb. 13, 2015, published in English, which claims priority from Australian Provisional Patent Application No. 2014900435, filed Feb. 13, 2014, all of which are incorporated herein by reference.

2 STATEMENT REGARDING FEDERALLY SPONSORED RESEARCH OR DEVELOPMENT

Not Applicable

3 THE NAMES OF PARTIES TO A JOINT RESEARCH DEVELOPMENT

Not Applicable

4 SEQUENCE LISTING

Not Applicable

5 BACKGROUND OF THE INVENTION 5.1 Field of the Invention

The present technology relates to one or more of the diagnosis, treatment, prevention, and amelioration of respiratory disorders. In particular, the present technology relates to medical devices, and their use for treating and preventing respiratory disorders.

5.2 Description of the Related Art

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See West, Respiratory Physiology—the essentials.

A range of respiratory disorders exist.

Obstructive Sleep Apnea (OSA), a form of Sleep Disordered Breathing (SDB), is characterized by occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is a form of periodic breathing that is due to a disorder of a patient's respiratory controller in which there are rhythmic alternating periods of waxing and waning ventilation during sleep, causing repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic nervous system activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

Otherwise healthy individuals may take advantage of systems and devices to prevent respiratory disorders from arising.

5.2.1 Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall.

Non-invasive ventilation (NIV) provides ventilator support to a patient through the upper airways to assist the patient in taking a full breath and/or maintain adequate oxygen levels in the body. The ventilator support is provided by a mask or nasal interface. NIV has been used to treat CSR, OHS, COPD, MD and Chest Wall disorders.

Invasive ventilation (IV) provides ventilatory support to patients that are no longer able to effectively breathe for themselves and is provided using a tracheostomy tube.

Ventilators also control the timing and pressure of breaths pumped into the patient and monitor the breaths taken by the patient. The methods of control and monitoring patients typically include volume-cycled and pressure-cycled methods. The volume-cycled methods may include among others, Pressure-Regulated Volume Control (PRVC), Volume Ventilation (VV), and Volume Controlled Continuous Mandatory Ventilation (VC-CMV) techniques. The pressure-cycled methods may involve, among others, Assist Control (AC), Synchronized Intermittent Mandatory Ventilation (SIMV), Controlled Mechanical Ventilation (CMV), Pressure Support Ventilation (PSV), Continuous Positive Airway Pressure (CPAP), or Positive End Expiratory Pressure (PEEP) techniques.

5.2.2 Systems

One known product used for treating sleep disordered breathing is the S9 Sleep Therapy System, manufactured by ResMed. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit.

5.2.3 Patient Interface

The application of a supply of air at positive pressure to the entrance of the airways of a patient is facilitated by the use of a patient interface, such as a nasal mask, full-face mask or nasal pillows. A range of patient interface devices are known, however a number of them suffer from being one or more of obtrusive, aesthetically undesirable, poorly fitting, difficult to use, and uncomfortable especially when worn for long periods of time or when a patient is unfamiliar with a system. Masks designed solely for aviators as part of personal protection equipment or for the administration of anaesthetics may be tolerable for their original application, but nevertheless be undesirably uncomfortable to be worn for extended periods, for example, while sleeping or throughout the day.

A tracheostomy tube is another form of patient interface that may be used for invasive ventilation.

5.2.4 PAP Device

The air at positive pressure may be supplied to the airway of a patient by a PAP device such as a motor-driven blower. The outlet of the blower is connected via a flexible delivery conduit to a patient interface as described above.

Ventilators typically include a flow generator or blower, an inlet filter, a patient interface, an air delivery conduit connecting the flow generator to the patient interface, various sensors and a microprocessor-based controller. The patient interface may include a mask or a tracheostomy tube as described above. The flow generator may include a servo-controlled motor, volute and an impeller that forms a blower. In some cases a brake for the motor may be implemented to more rapidly reduce the speed of the blower so as to overcome the inertia of the motor and impeller. The braking can permit the blower to more rapidly achieve a lower pressure condition in time for synchronization with expiration despite the inertia. In some cases the flow generator may also include a valve capable of discharging generated air to atmosphere as a means for altering the pressure delivered to the patient as an alternative to motor speed control. The sensors measure, amongst other things, motor speed, mass flow rate and outlet pressure, such as with a pressure transducer or the like. The apparatus may optionally include a humidifier and/or heater elements in the path of the air delivery circuit. The controller may include data storage capacity with or without integrated data retrieval and display functions.

5.2.5 Monitoring Systems

The clinical significance of CSR is substantial, and it is therefore important to know how much CSR is present during sleep. In particular, it can be useful to know if patients on CPAP therapy are exhibiting CSR because there is a potential for improved therapy with, for example, an adaptive servo-ventilator (ASV) device. Alternatively, the patient can be further monitored to see whether the CSR persists or whether it was a result of so-called CPAP-emergent central sleep apnea (CSA).

The diagnosis of CSR usually involves conducting a sleep study, and analyzing the resulting polysomnography ("PSG") data. In a full diagnostic PSG study, a range of biological parameters are monitored that typically include a nasal flow signal, measures of respiratory effort, pulse oximetry, sleeping position, and may further include: electroencephalography ("EEG"), electrocardiography ("ECG"), electromyography ("EMG"), and electro-oculography ("EOG"). Breathing characteristics such as CSR may be identified from visual features of the above-mentioned parameters, thus allowing a clinician to assess respiratory function during sleep and detect and measure any episodes of CSR.

While examination by a clinician is the most comprehensive method, it is a costly process and depends heavily upon clinical experience and understanding. For efficient screening of patients, a classifier-based method has been developed that automates the scoring process by calculating the probability of CSR occurring at regular intervals based on a nasal flow signal. The method is disclosed in U.S. patent application Ser. No. 11/576,210 (U.S. Patent App. Pub. No. 20080177195) filed 28 Mar. 2007, and published as WO2006066337A1 on 29 Jun. 2006. The method includes a flow-based classifier where a probability of CSR is calculated given a sequence of discrete flow values. The method described in WO2006066337A1 uses a multidimensional feature space and performs cluster analysis by using discriminant functions to separate the features into clusters. This approach is computationally intensive and is therefore typically performed on a computing device that is separate from the therapy device, using a batch of data that has been recorded over a complete therapy or monitoring session.

Another method, disclosed in PCT patent application no. PCT/AU2013/000063 and published as WO2013110136 on 1 Aug. 2013, is also carried out on data recorded over a complete monitoring or therapy session. The method of WO2013110136 partitions the flow data into intervals based on SDB events such as apneas and hypopneas, and constructs a histogram of interval lengths to determine whether CSR was present during the session. Shape features of the data are also extracted and used to label intervals as containing CSR. Again, this method is most suitable for "batch mode" analysis at the conclusion of a session.

A need exists for a more immediate method of detecting CSR episodes, preferably one that operates "on the fly" during a monitoring or therapy session based only on recent data, that is, in "real time" as opposed to "batch mode". This would allow immediate action to be taken in response to the CSR episode before it is even concluded, such as a change to therapy parameters or the issuing of an alert to a clinician.

6 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to a device used in the diagnosis, amelioration, treatment or prevention of a respiratory disorder.

Another aspect of the present technology relates to methods used in the diagnosis, amelioration, treatment or prevention of a respiratory disorder.

One form of the present technology comprises a device that determines in "real time" whether to signal that an episode of periodic breathing, such as Cheyne-Stokes respiration, has started or ended, based on an analysis of SDB events such as apneas and hypopneas.

Another aspect of one form of the present technology is a method of analysing SDB events such as apneas and hypopneas so as to determine the start and end times of periodic breathing episodes as, or soon after, they occur.

According to a first aspect of the present technology, there is provided a method of detecting periodic breathing in a patient, the method comprising: receiving in a processor a series of event intervals bounded by apnea or hypopnea events detected in the respiration of the patient; processing, upon closure of an event interval, the event interval to determine a character of the event interval, wherein the character of an event interval is one of: probably a periodic breathing cycle; probably not a periodic breathing cycle; and uninformative; and determining in the processor whether to change a current periodic breathing state that indicates whether a periodic breathing episode is in progress, based on a history of event interval characters that is long compared to the typical length of a periodic breathing cycle.

According to another aspect of the present technology, there is provided a device for detecting periodic breathing in a patient, the device comprising: a sensor configured to provide a signal representing respiratory airflow of the patient; and a processor configured to carry out a method including receiving in a processor a series of event intervals bounded by apnea or hypopnea events detected in the respiration of the patient; processing, upon closure of an event interval, the event interval to determine a character of the event interval, wherein the character of an event interval is one of: probably a periodic breathing cycle; probably not a periodic breathing cycle; and uninformative; and determining in the processor whether to change a current periodic breathing state that indicates whether a periodic breathing episode is in progress, based on a history of event interval characters that is long compared to the typical length of a periodic breathing cycle.

According to yet another aspect of the present technology, there is provided a computer-readable storage medium on which are stored program code instructions configured to cause a processor to carry out a method including receiving in a processor a series of event intervals bounded by apnea or hypopnea events detected in the respiration of the patient; processing, upon closure of an event interval, the event interval to determine a character of the event interval, wherein the character of an event interval is one of: probably a periodic breathing cycle; probably not a periodic breathing cycle; and uninformative; and determining in the processor whether to change a current periodic breathing state that indicates whether a periodic breathing episode is in progress, based on a history of event interval characters that is long compared to the typical length of a periodic breathing cycle.

Some versions of the present technology may involve a method, such as in one or more processors, for detecting periodic breathing by a patient. The method may include receiving in a processor a series, such as a data series, of event intervals bounded by apnea or hypopnea events detected in respiration of the patient. The method may include processing in a processor, upon closure of an event interval, the event interval to determine a character of the event interval, wherein the character of an event interval is one of: probably a periodic breathing cycle; probably not a periodic breathing cycle; and uninformative. The method may also include determining in a processor whether to change a current periodic breathing state that indicates whether a periodic breathing episode is in progress, based on a history of event interval characters that is long compared to a typical length of a periodic breathing cycle.

In some cases, the method may also include reporting a parameter of a detected periodic breathing episode. The patient may be undergoing therapy for a breathing disorder such that the method may also include adjusting one or more parameters of the therapy in response to a detected periodic breathing episode. In some versions of the method, the processing may be dependent on a sequence of measures of breathwise ventilation associated with the event interval. The measure of breathwise ventilation may be a product of a magnitude of a current half-breath and a magnitude of a previous half-breath. The magnitude of a half-breath may be a tidal volume of the half-breath. Optionally, the processing may include determining that the event interval was probably not a periodic breathing cycle if a duration of the event interval is outside a range of a typical periodic breathing cycle, or the sequence of measures of breathwise ventilation contains fewer than a minimum number of non-zero measures of breathwise ventilation. Optionally, the processing may further include computing a relative maximum step feature from the sequence of measures of breathwise ventilation.

The processing may further include, in a case of the event interval being closed by a hypopnea event: constructing a template representing an expected sequence of breathwise ventilation measures consistent with the event interval being a lead-up to a periodic breathing hypopnea; computing a difference between the sequence of breathwise ventilation measures and the template; and determining the character of the event interval based on the relative maximum step feature and the difference. In some cases, the determining may include: determining that the event interval was probably not a periodic breathing cycle if the relative maximum step feature exceeds a first threshold; and determining that the event interval was probably a periodic breathing cycle if the difference is less than a second threshold and a duration of the event interval is greater than a third threshold. Optionally, the processing may include, in a case of the event interval being closed by an apnea event: constructing a template representing an expected sequence of breathwise ventilation measures consistent with the event interval being a lead-up to an obstructive sleep apnea; constructing a template representing an expected sequence of breathwise ventilation measures consistent with the event interval being a lead-up to a periodic breathing apnea; computing differences between the sequence of breathwise ventilation measures and each template; computing a periodic breathing similarity score from the differences; and determining the character of the event interval based on the relative maximum step feature and the periodic breathing similarity score.

In some cases, the determining may include determining that the event interval was probably not a periodic breathing cycle if the relative maximum step feature exceeds a first threshold; and determining that the event interval was probably a periodic breathing cycle if the periodic breathing similarity score is greater than a second threshold and a duration of the event interval is greater than a third threshold. In some cases, the determining may include: computing a count of event intervals in the history that were probably periodic breathing cycles, a count of event intervals in the history that were probably not periodic breathing cycles, and a total count of event intervals in the history; changing the periodic breathing state to true if the counts meet start criteria; and changing the periodic breathing state to false if the counts meet end criteria. The determining may include changing the periodic breathing state to false if the event interval was closed by a timeout. Optionally, in some cases, the method may also include, such as upon changing the periodic breathing state to true, adjusting a start time of a just-started periodic breathing episode. In some cases the method may include, such as upon changing the periodic breathing state to false, adjusting an end time of a just-ended periodic breathing episode.

Some versions of the present technology may include a device for detecting periodic breathing in a patient. The device may include a sensor configured to provide a signal representing respiratory airflow of the patient. The device may include a processor configured to detect periodic breathing in a patient. The processor may be configured to receive a series of event intervals bounded by apnea or hypopnea events detected in the respiration of the patient using the signal from the sensor. The processor may be configured to process, upon closure of an event interval, the event interval to determine a character of the event interval, wherein the character of an event interval is one of: probably a periodic breathing cycle; probably not a periodic breathing cycle; and uninformative. The processor may be configured to determine whether to change a current periodic breathing state that indicates whether a periodic breathing episode is in progress, based on a history of event interval characters that is long compared to a typical length of a periodic breathing cycle.

In some cases, the device may also include a therapy device configured to provide therapy to the patient for a breathing disorder, and, for example, the processor may be further configured to adjust one or more parameters of the therapy in response to a detected periodic breathing episode. Optionally, the device may include a data communication interface coupled with the processor, and the processor may be further configured to report a parameter of a detected periodic breathing episode through the data communication interface to an external device.

The device may further include a processor configured to control any one or more of the features of the methodologies described previously or throughout this specification.

Some versions of the present technology may include a computer-readable storage medium on which are stored program code instructions configured to cause a processor to carry out a method of detecting periodic breathing in a patient. The method may include providing receiving a series of event intervals bounded by apnea or hypopnea events detected in respiration of the patient. The method may include processing, upon closure of an event interval, the event interval to determine a character of the event interval, wherein the character of an event interval is one of: probably a periodic breathing cycle; probably not a periodic breathing cycle; and uninformative. The method may include determining whether to change a current periodic breathing state that indicates whether a periodic breathing episode is in progress, based on a history of event interval characters that is long compared to a typical length of a periodic breathing cycle. Any one or more additional optional features of the method may include the features of the methodologies described previously or throughout this specification.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

7 BRIEF DESCRIPTION OF THE SEVERAL VIEWS OF THE DRAWINGS

The present technology is illustrated by way of example, and not by way of limitation, in the figures of the accompanying drawings, in which like reference numerals refer to similar elements including:

7.1 Treatment Systems

FIG. 1 shows a system in accordance with one form of the present technology. A patient 1000 wearing a patient interface 3000 receives a supply of air at positive pressure from a PAP device 4000. Air from the PAP device is humidified in a humidifier 5000, and passes along an air circuit 4170 to the patient 1000. A bed partner 1100 is also shown.

7.2 Respiratory System

FIG. 2 shows an overview of a human respiratory system including the nasal and oral cavities, the larynx, vocal folds, oesophagus, trachea, bronchus, lung, alveolar sacs, heart and diaphragm.

7.3 Patient Interface

FIG. 3 shows a patient interface 3000 in accordance with one form of the present technology.

7.4 PAP Device

7.5 Humidifier

Figure 5:
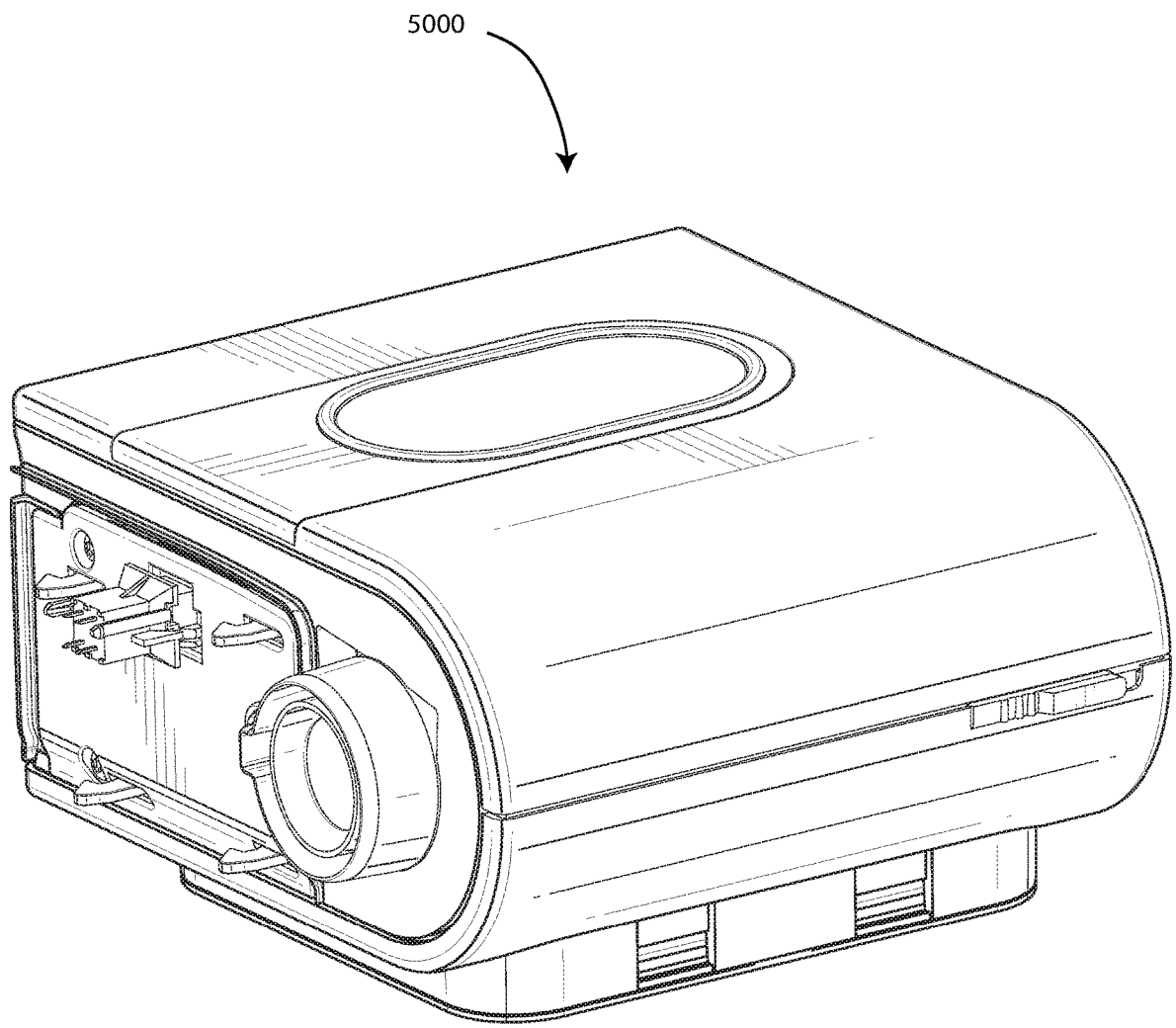

FIG. 5 shows a humidifier 5000 in accordance with one aspect of the present technology.

7.6 Breathing Waveforms

Figure 6A:
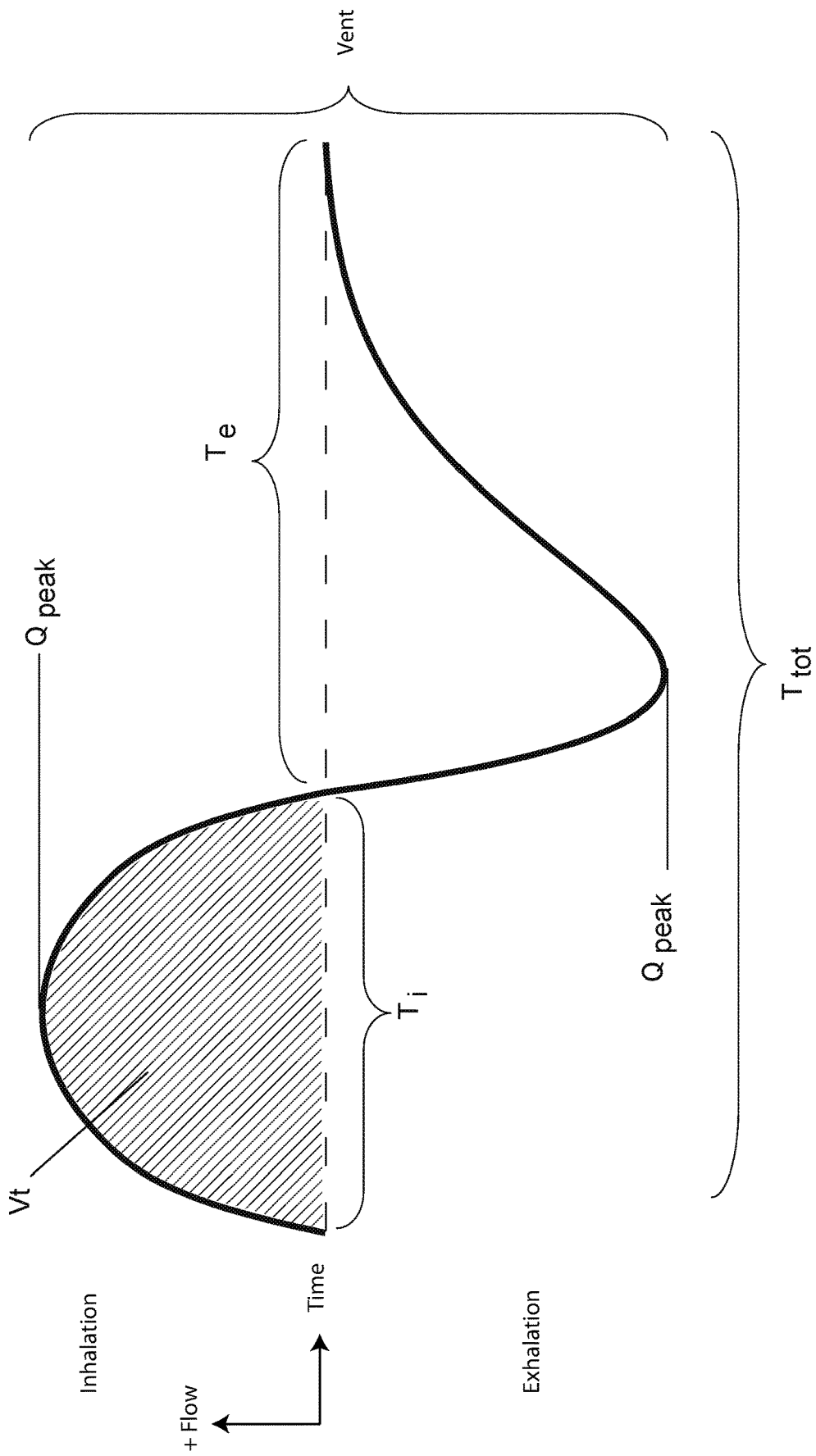

FIG. 6A shows a model typical breath waveform of a person while sleeping. The horizontal axis is time, and the vertical axis is respiratory flow. While the parameter values may vary, a typical breath may have the following approximate values: tidal volume, Vt, 0.5 L, inhalation time, Ti, 1.6 s, peak inspiratory flow, Qpeak, 0.4 L/s, exhalation time, Te, 2.4 s, peak expiratory flow, Qpeak, −0.5 L/s. The total duration of the breath, Ttot, is about 4 s. The person typically breathes at a rate of about 15 breaths per minute (BPM), with Ventilation, Vent, about 7.5 L/minute. A typical duty cycle, the ratio of Ti to Ttot, is about 40%.

Figure 6B:
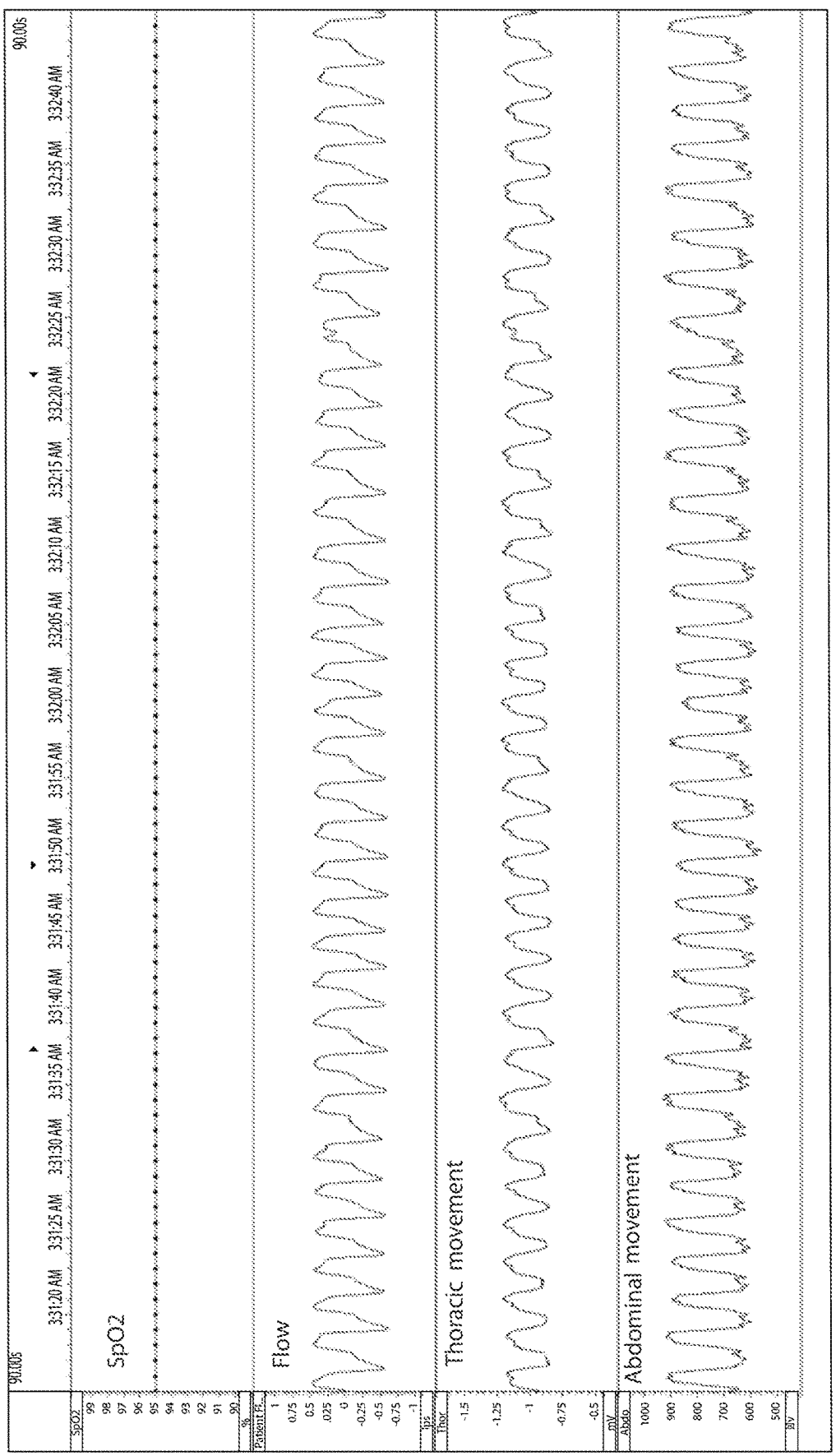

FIG. 6B shows data from a patient during non-REM sleep breathing normally over a period of about ninety seconds, with about 34 breaths, being treated with Automatic PAP, and the mask pressure being about 11 cmH$_2$O. The top channel shows oximetry (SpO$_2$), the scale has a range of saturation from 90 to 99% in the vertical direction. The patient maintained a saturation of about 95% throughout the period shown. The second channel shows quantitative respiratory airflow, and the scale ranges from −1 to +1 L/s in a vertical direction, and with inspiration positive. Thoracic and abdominal movement are shown in the third and fourth channels.

Figure 6C:
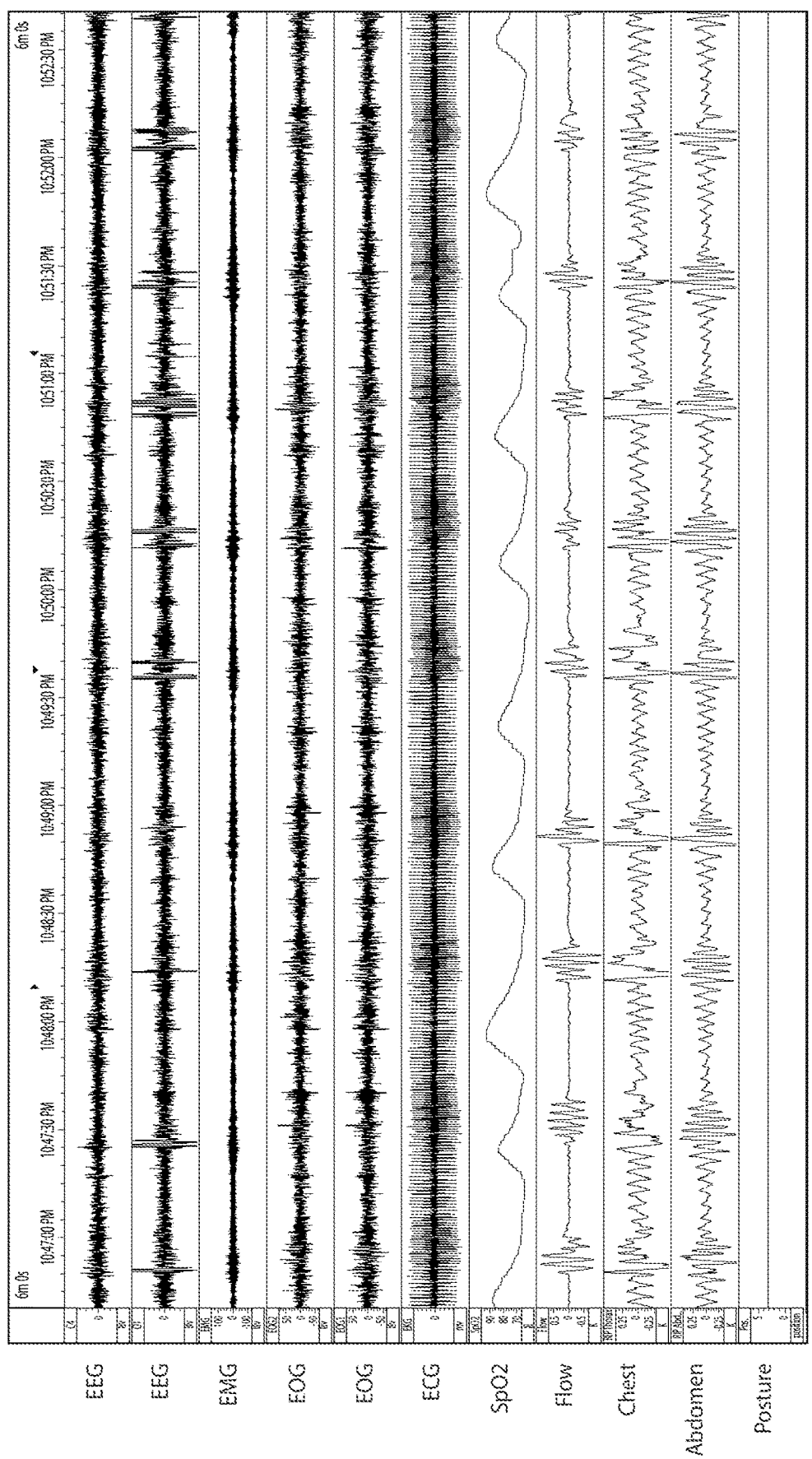

FIG. 6C shows polysomnography of a patient before treatment. There are eleven signal channels from top to bottom with a 6 minute horizontal span. The top two channels are both EEG (electoencephalogram) from different scalp locations. Periodic spikes in the second EEG represent cortical arousal and related activity. The third channel down is submental EMG (electromyogram). Increasing activity around the time of arousals represents genioglossus recruitment. The fourth & fifth channels are EOG (electro-oculogram). The sixth channel is an electocardiogram. The seventh channel shows pulse oximetry (SpO$_2$) with repetitive desaturations to below 70% from about 90%. The eighth channel is respiratory airflow using a nasal cannula connected to a differential pressure transducer. Repetitive apneas of 25 to 35 seconds alternate with 10 to 15 second bursts of recovery breathing coinciding with EEG arousal and increased EMG activity. The ninth channel shows movement of chest and the tenth channel shows movement of abdomen. The abdomen shows a crescendo of movement over the length of the apnea leading to the arousal. Both become untidy during the arousal due to gross body movement during recovery hyperpnea. The apneas are therefore obstructive, and the condition is severe. The lowest channel is posture, and in this example it does not show change.

Figure 6D:
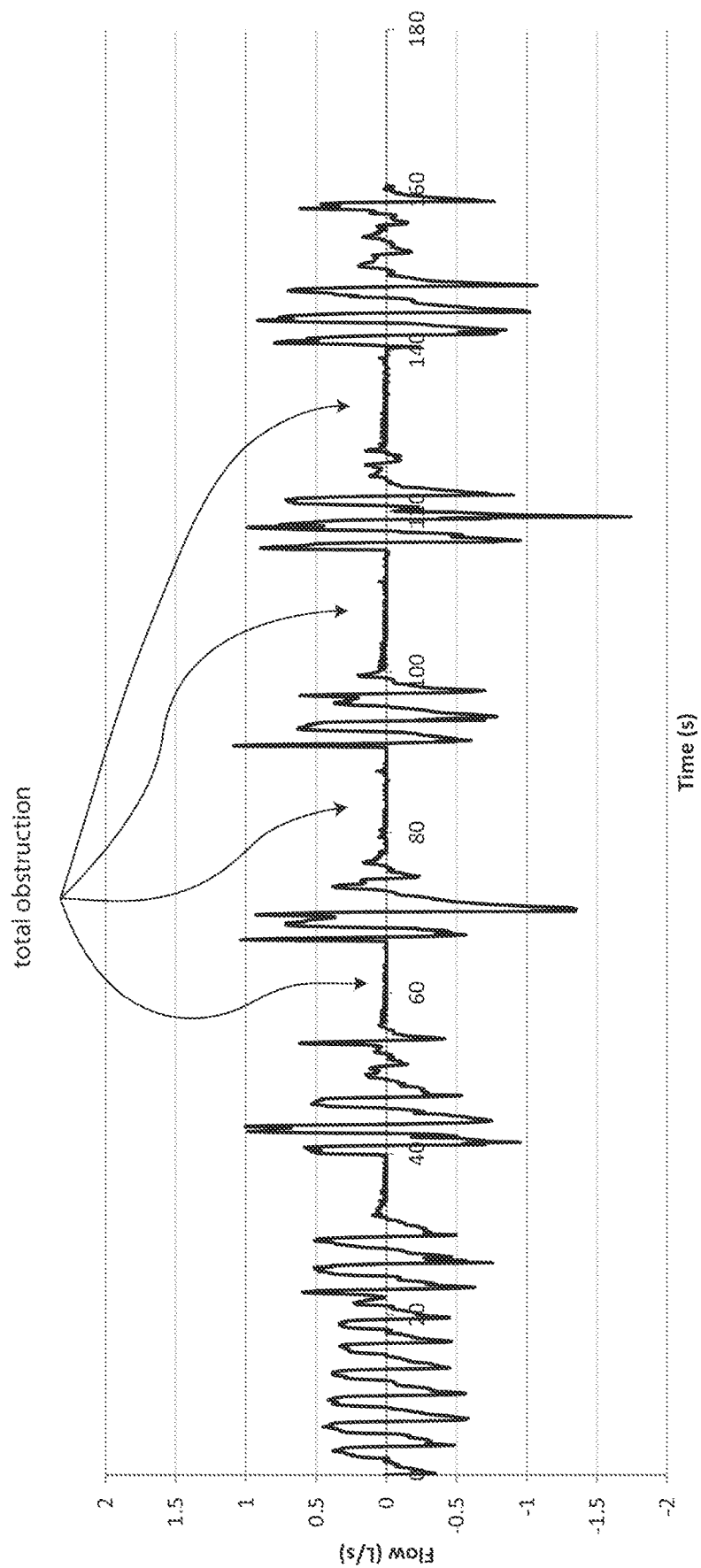

FIG. 6D shows patient flow data where the patient is experiencing a series of total obstructive apneas. The duration of the recording is approximately 160 seconds. Flow ranges from about +1 L/s to about −1.5 L/s. Each apnea lasts approximately 10-15 seconds.

Figure 6E:
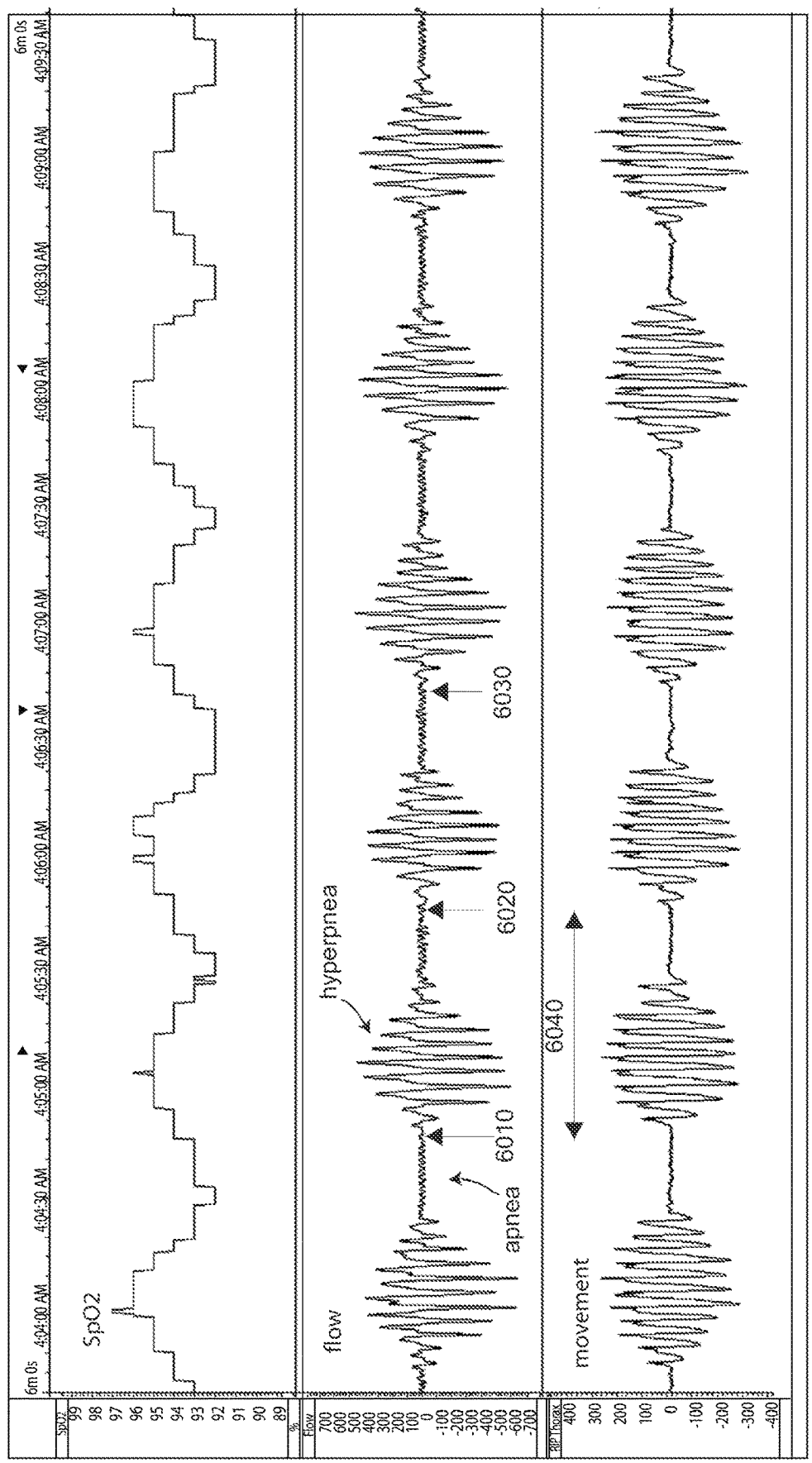

FIG. 6E shows data from a patient with Cheyne-Stokes respiration. There are three channels—oxygen saturation (SpO$_2$), a signal indicative of flow, and movement. The data span six minutes. The signal indicative of flow was measured using a pressure sensor connected to nasal cannulae. The patient exhibits apneas of about 22 seconds and hyperpneas of about 38 seconds. The higher frequency low amplitude oscillation during apnea is cardiogenic.

Figure 6F:
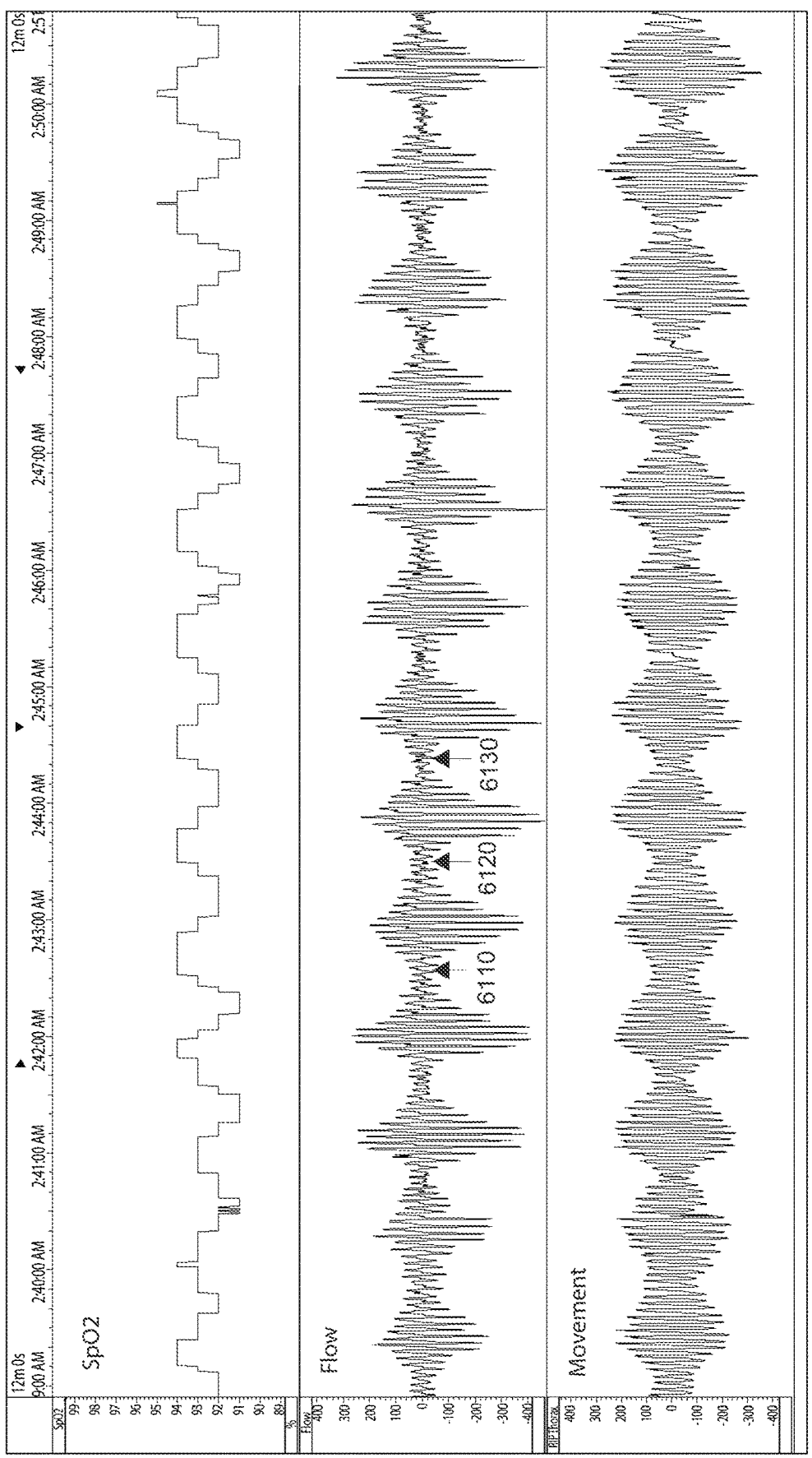

FIG. 6F shows data from a patient with another example of Cheyne-Stokes respiration, using the same three channels as in FIG. 6E. The data span ten minutes. The patient exhibits hypopneas of about 30 seconds and hyperpneas of about 30 seconds.

7.7 Monitoring Systems

Figure 7:
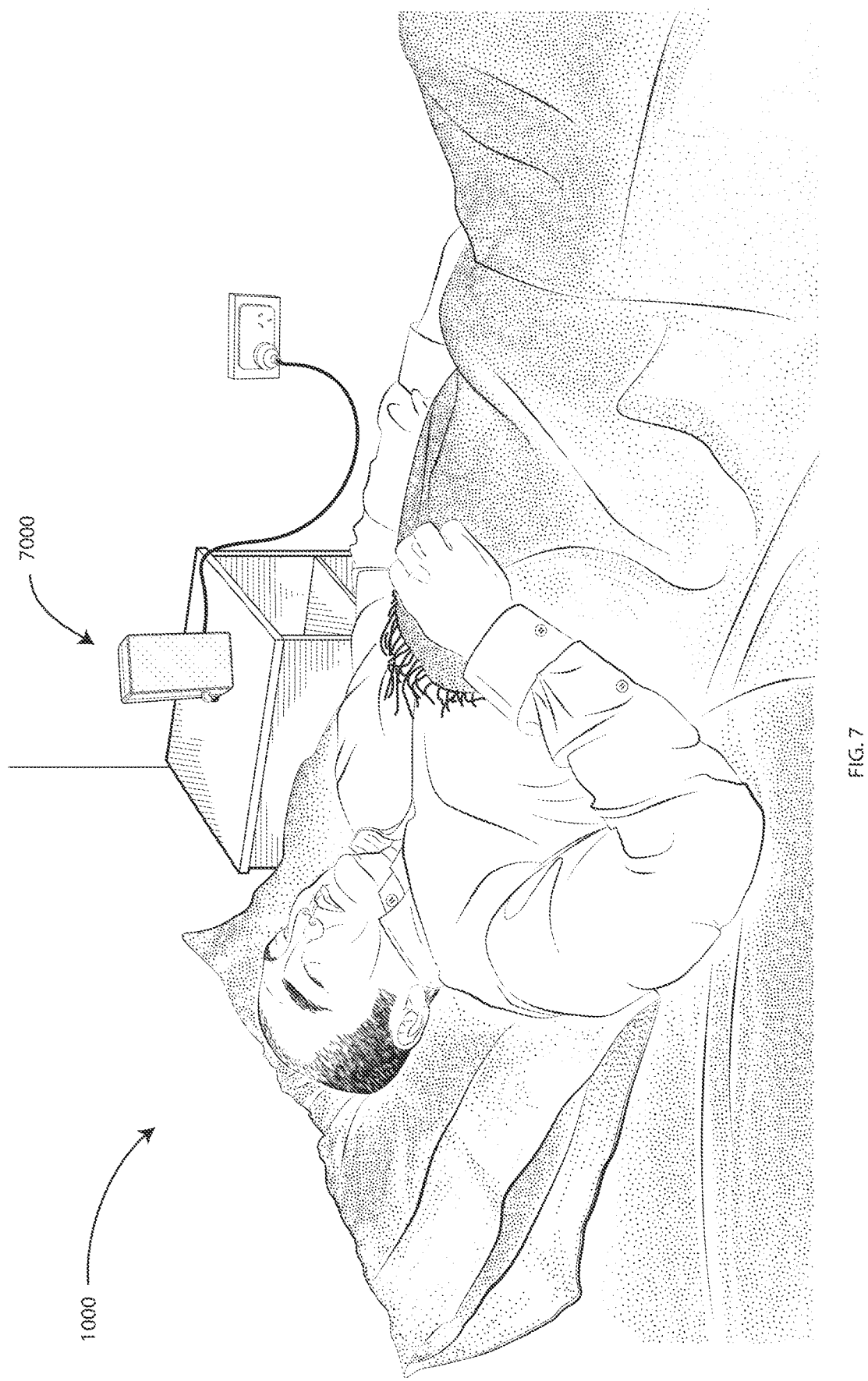

FIG. 7 shows a monitoring system in accordance with another form of the present technology. A patient 1000 is being monitored by a nearby non-contact movement sensor 7000.

Figure 1:
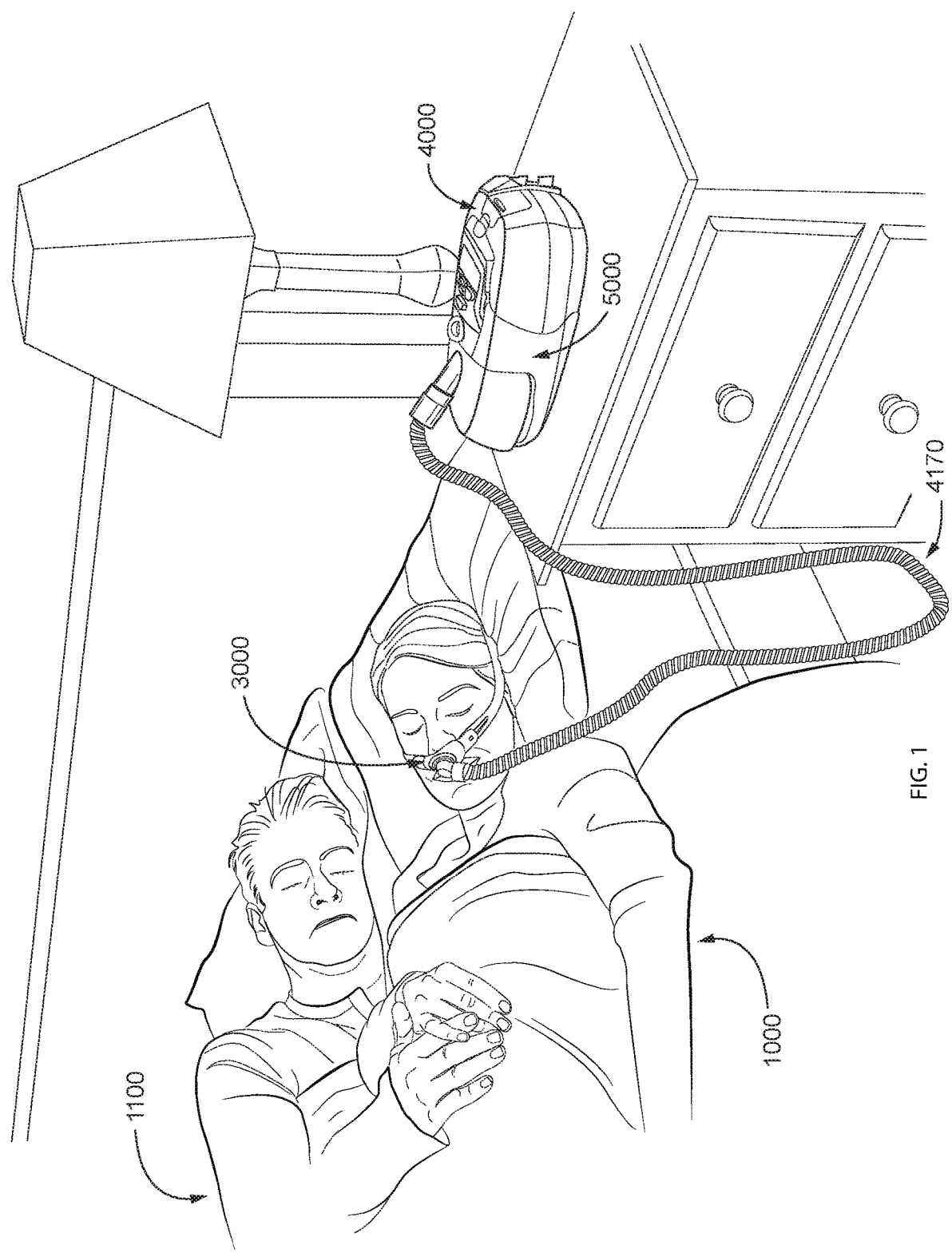
Figure 2:
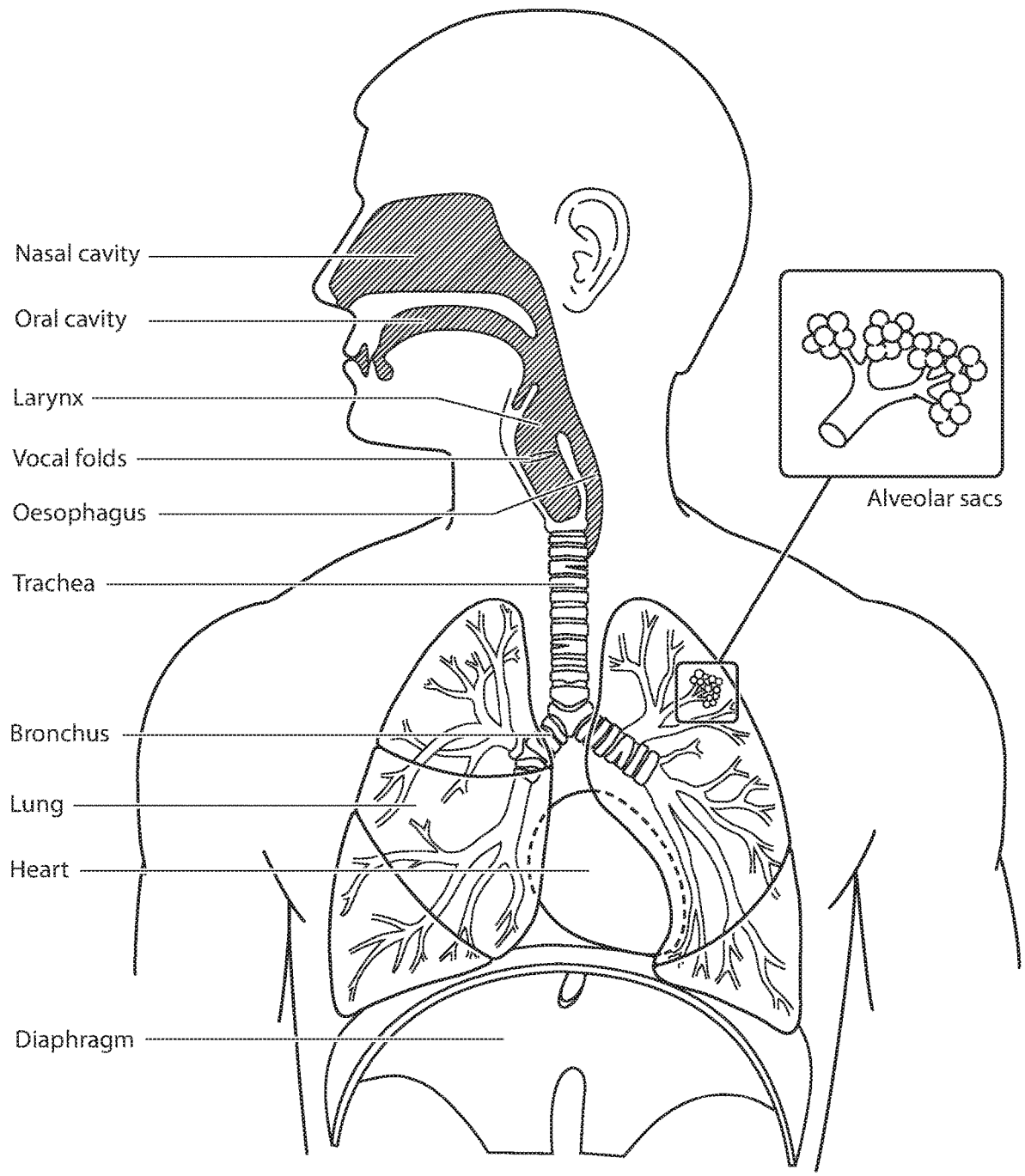
Figure 3:
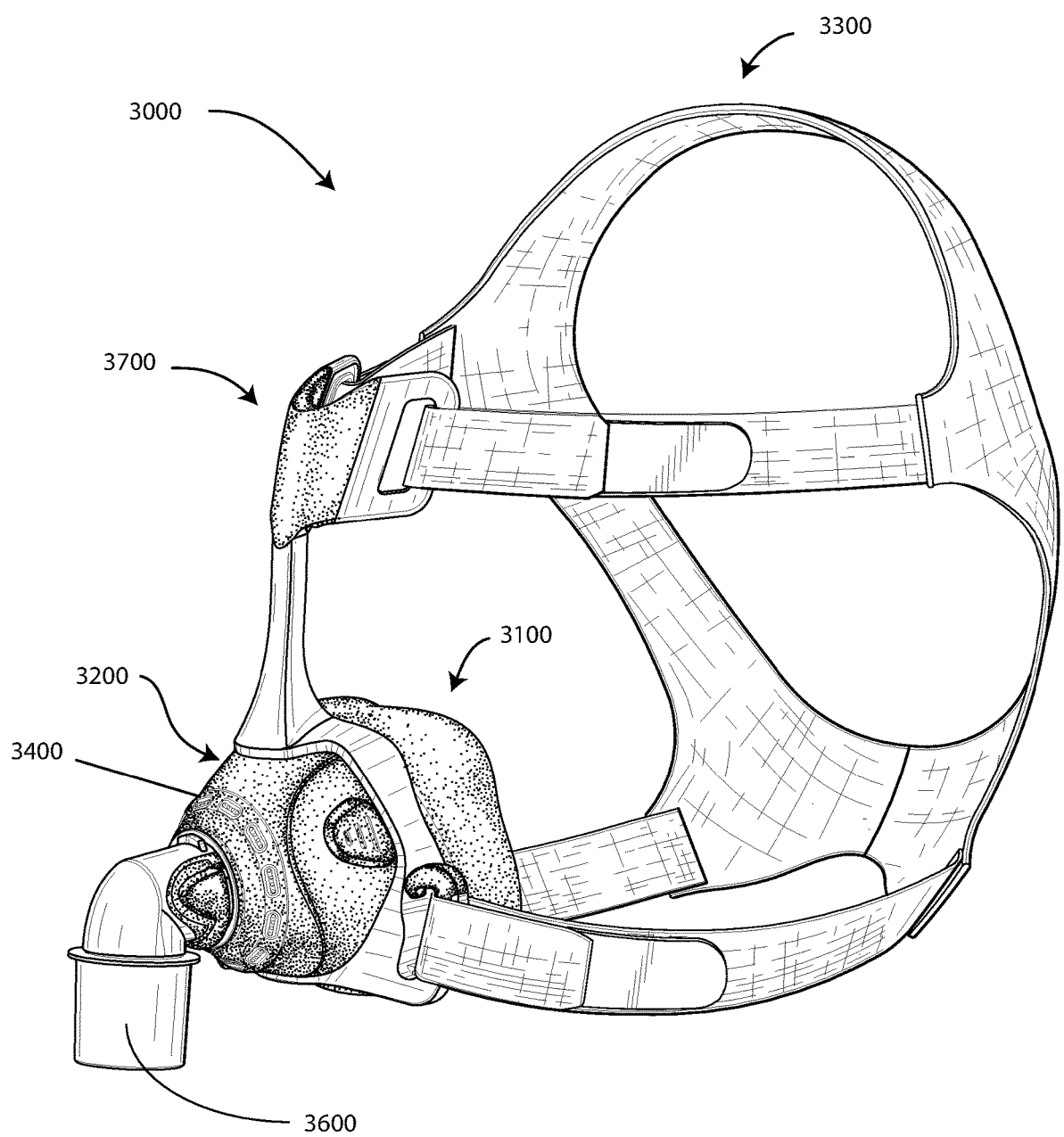
Figure 4A:
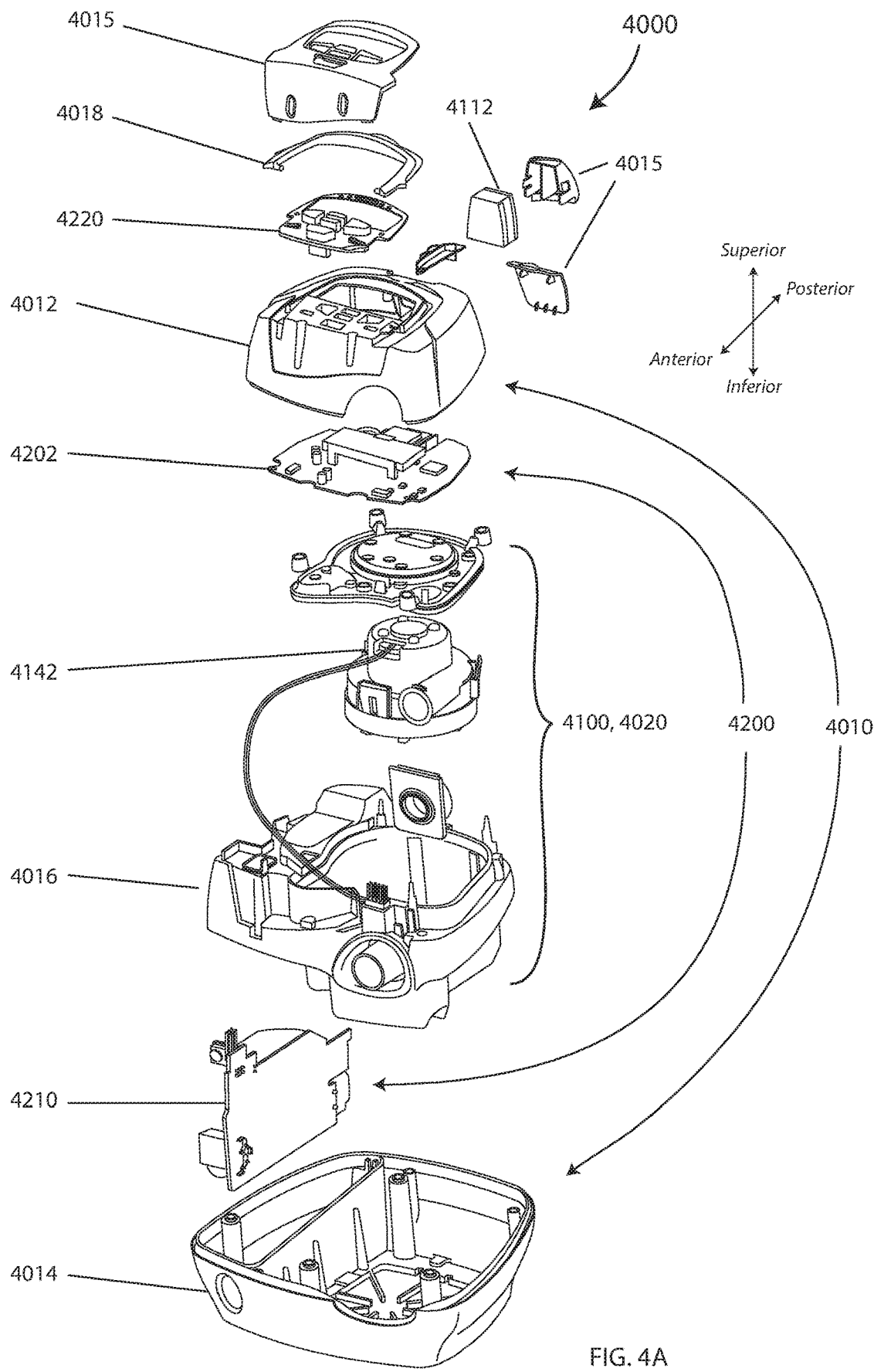
FIG. 4A shows a PAP device 4000 in accordance with one form of the present technology.
Figure 4B:
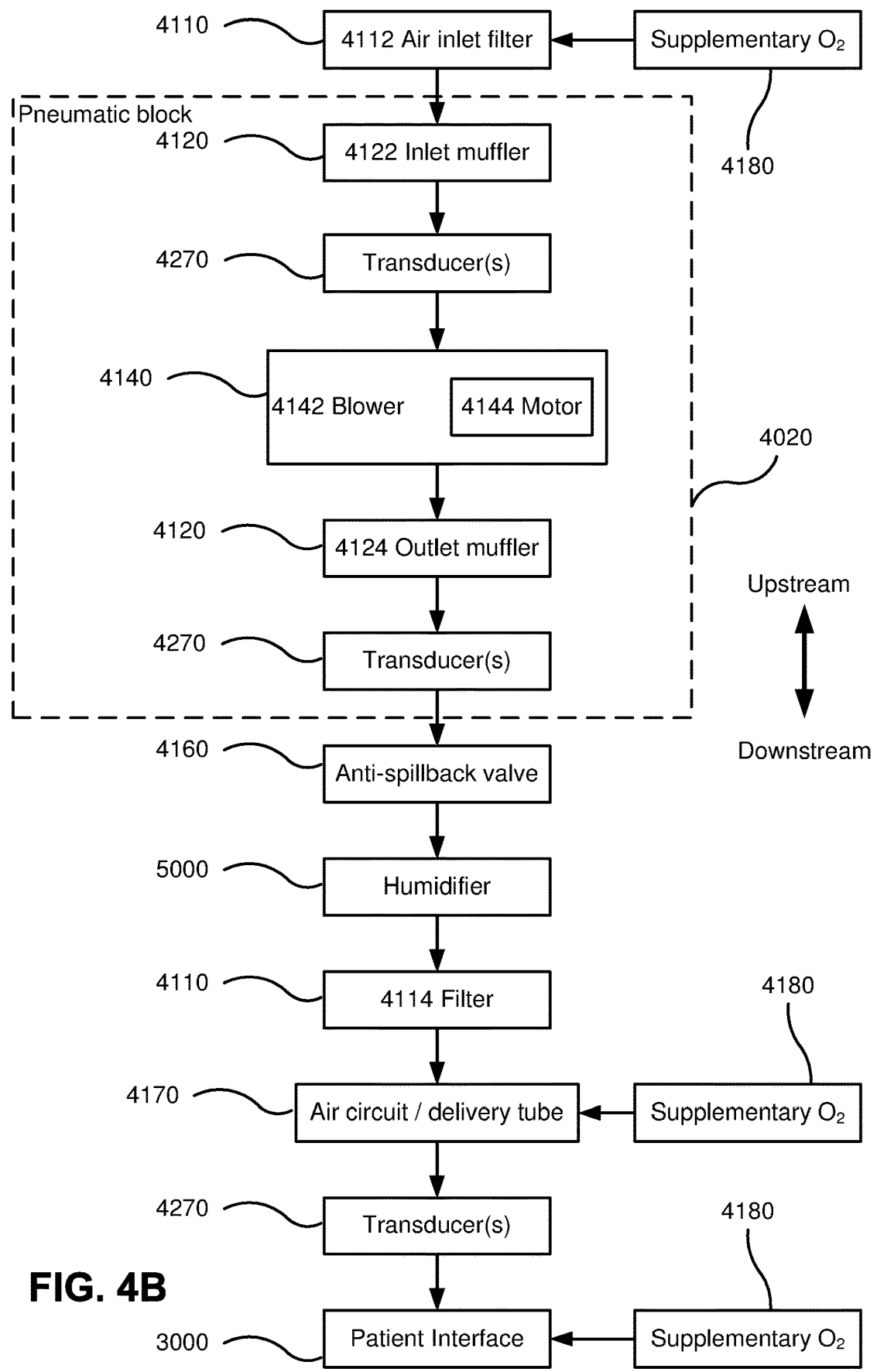
FIG. 4B shows a schematic diagram of the pneumatic circuit of a PAP device 4000 in accordance with one form of the present technology. The directions of upstream and downstream are indicated.
Figure 4C:
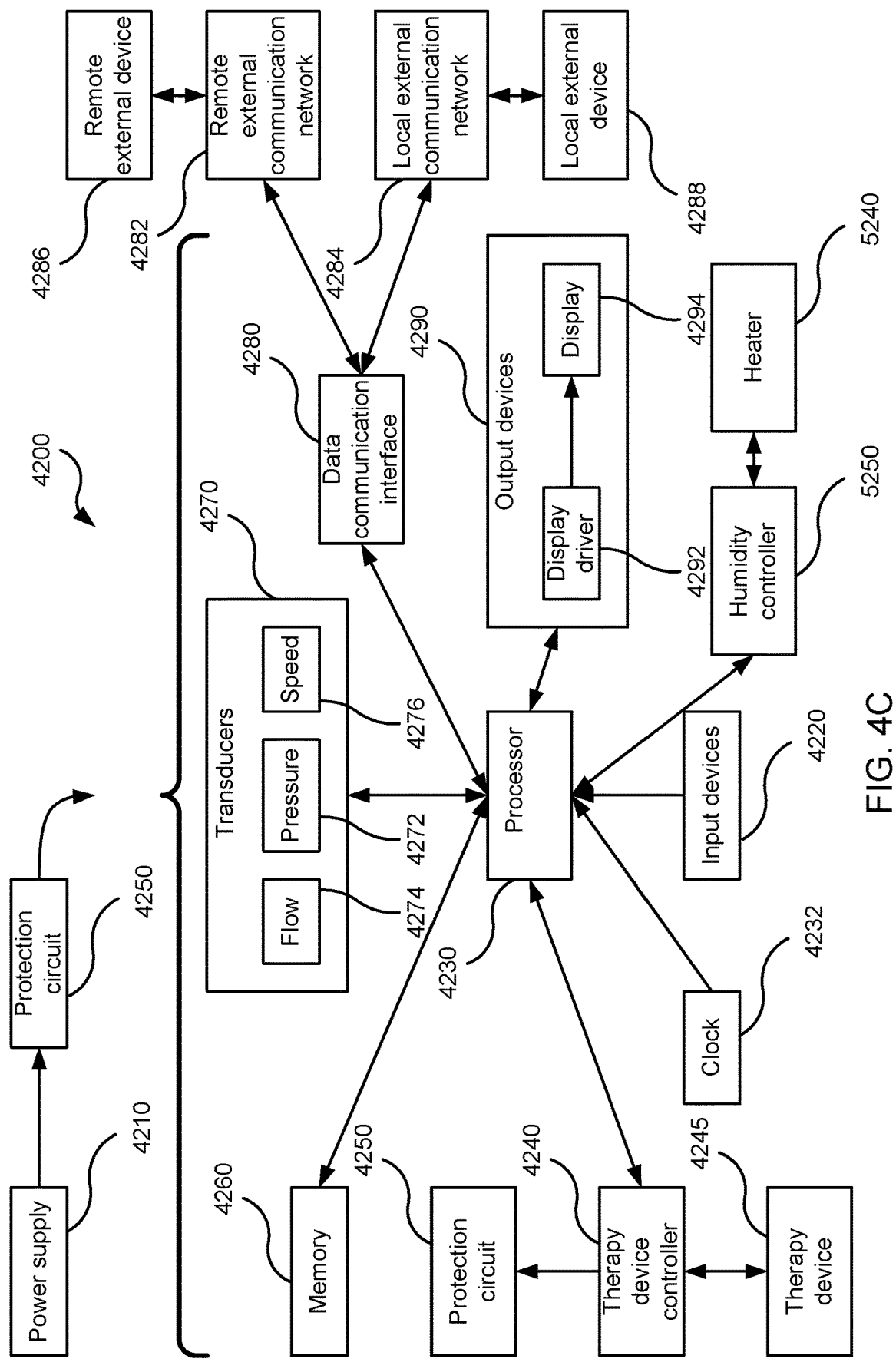
FIG. 4C shows a schematic diagram of the electrical components of a PAP device 4000 in accordance with one aspect of the present technology.
Figure 4D:
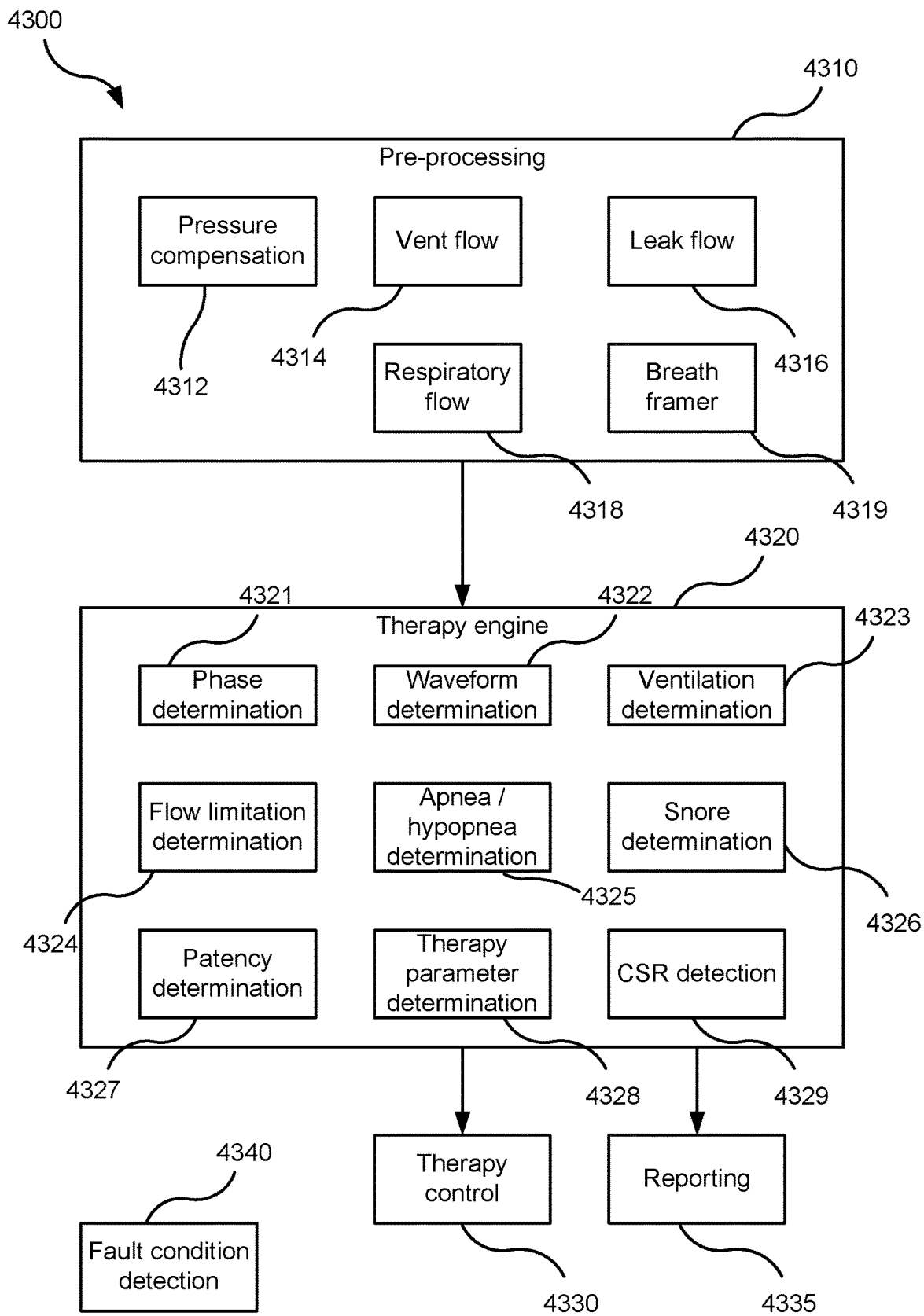
FIG. 4D shows a schematic diagram of the algorithms 4300 implemented in a PAP device 4000 in accordance with an aspect of the present technology.
Figure 8:
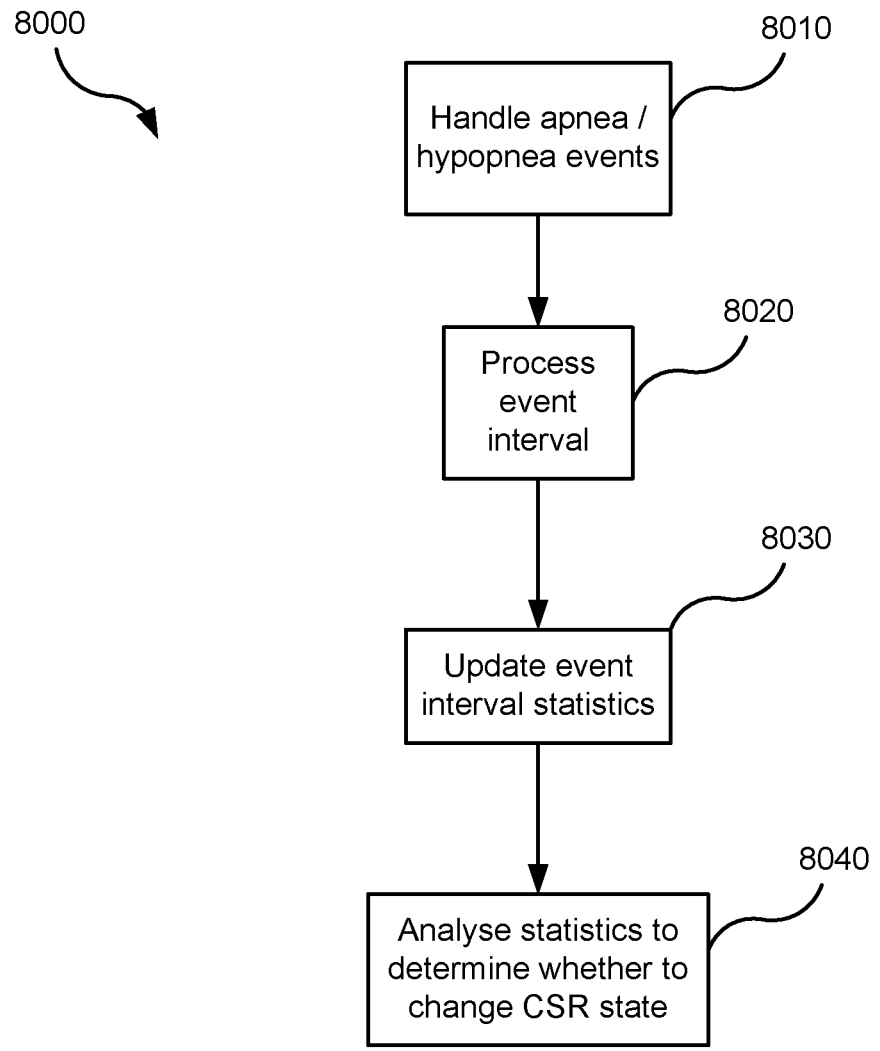

FIG. 8 contains a flow chart illustrating a method that may be used to implement the Cheyne-Stokes Respiration detection algorithm of FIG. 4D in one form of the present technology.

Figure 9:
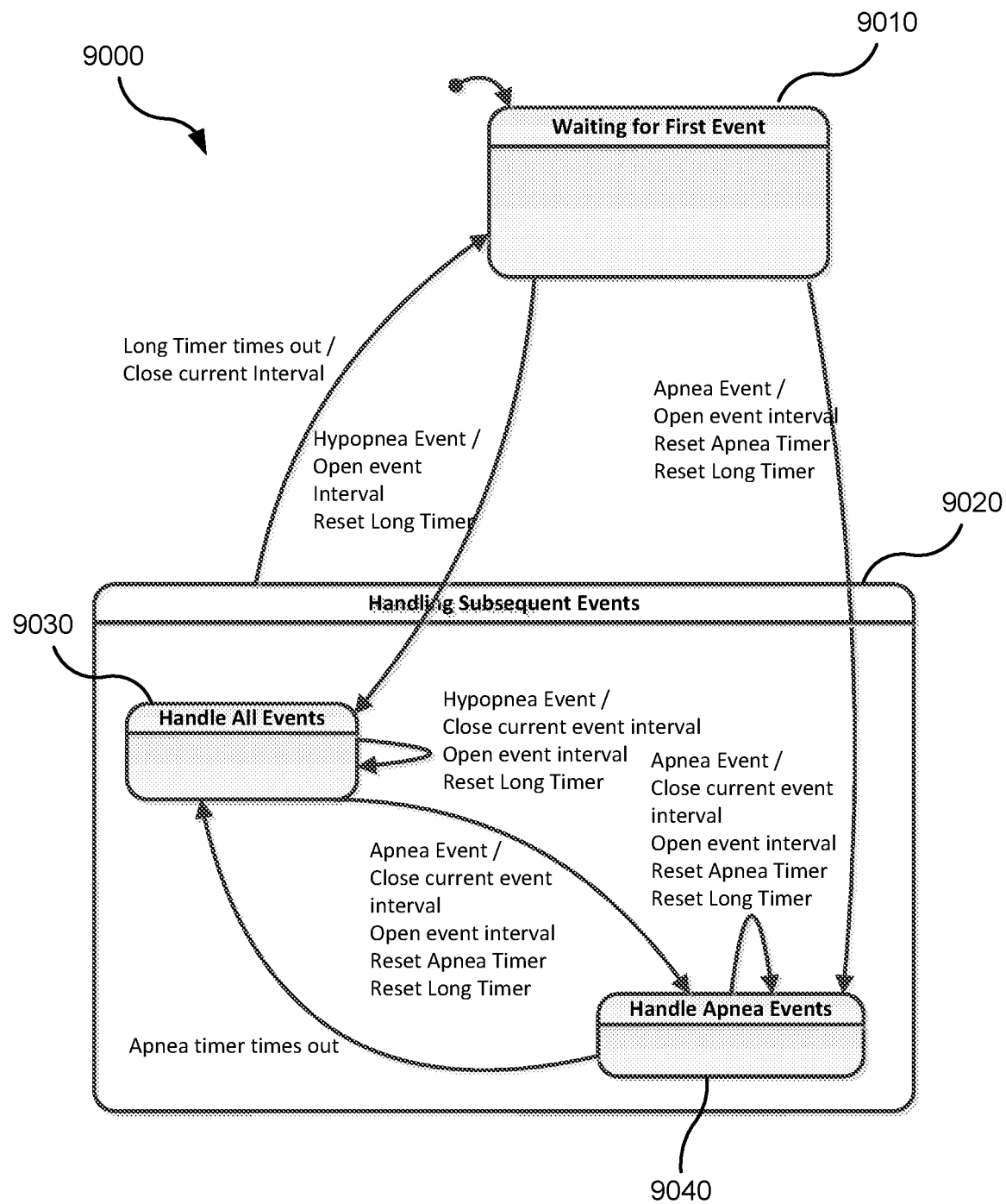

FIG. 9 is a diagram of a hierarchical state machine that may be used to implement the event handler of the method of FIG. 8 in one form of the present technology.

Figure 10:
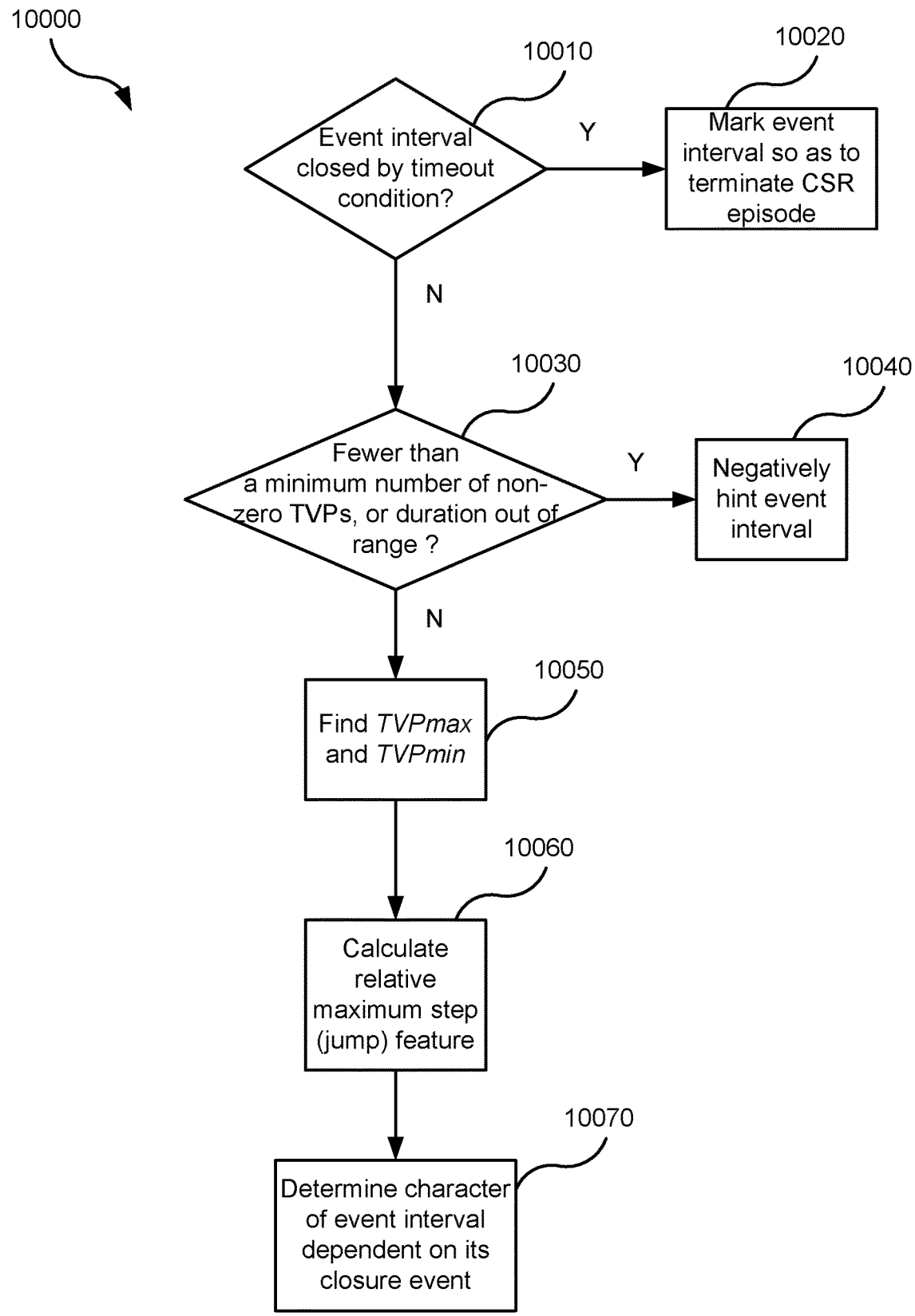

FIG. 10 contains a flow chart illustrating a method that may be used to implement the event interval-processing step of the method of FIG. 8 in one form of the present technology.

Figure 11:
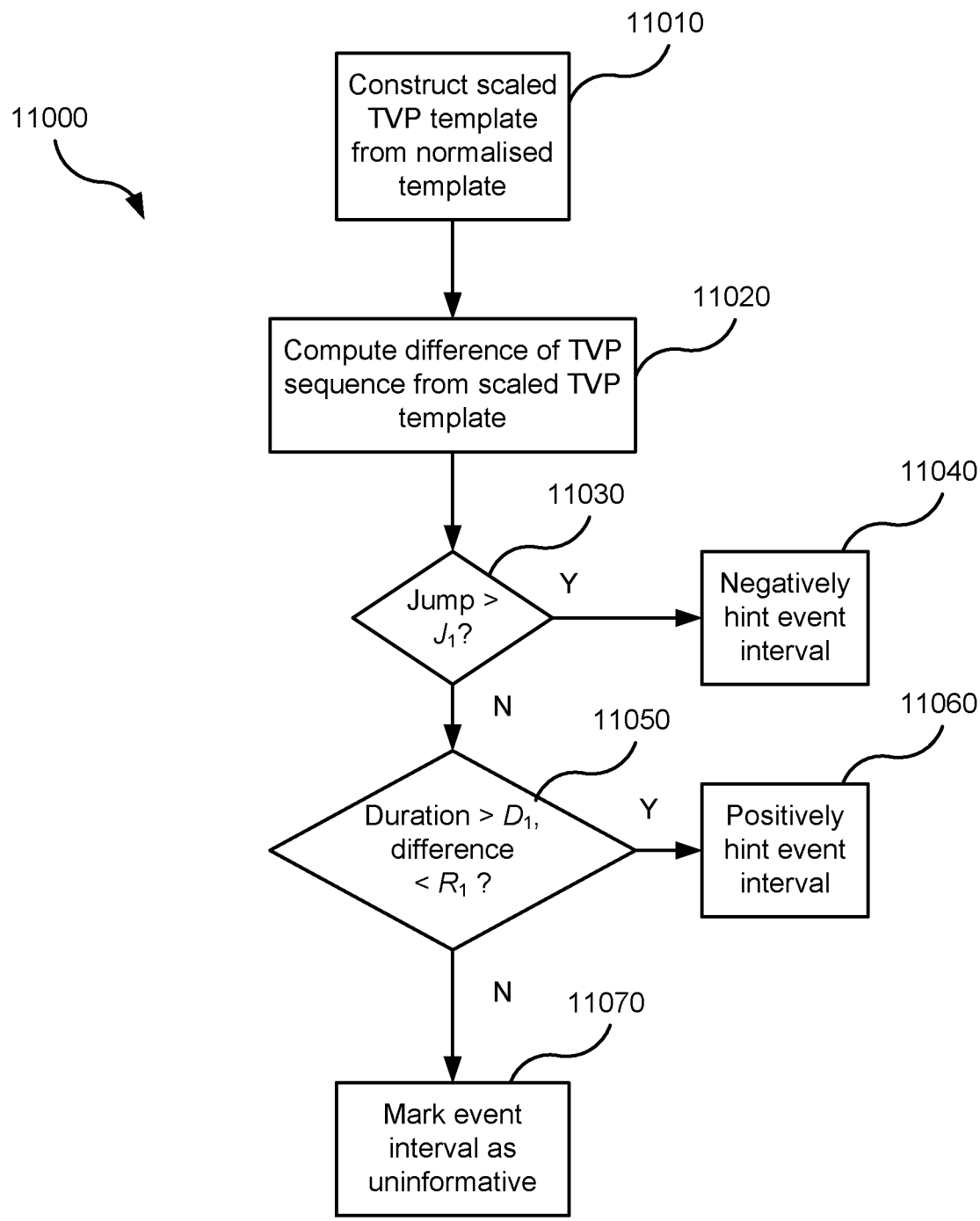

FIG. 11 contains a flow chart illustrating a method that may be used to implement the character determination step of the method of FIG. 10 in the case where the event interval was closed by a hypopnea event, in one form of the present technology.

Figure 12:
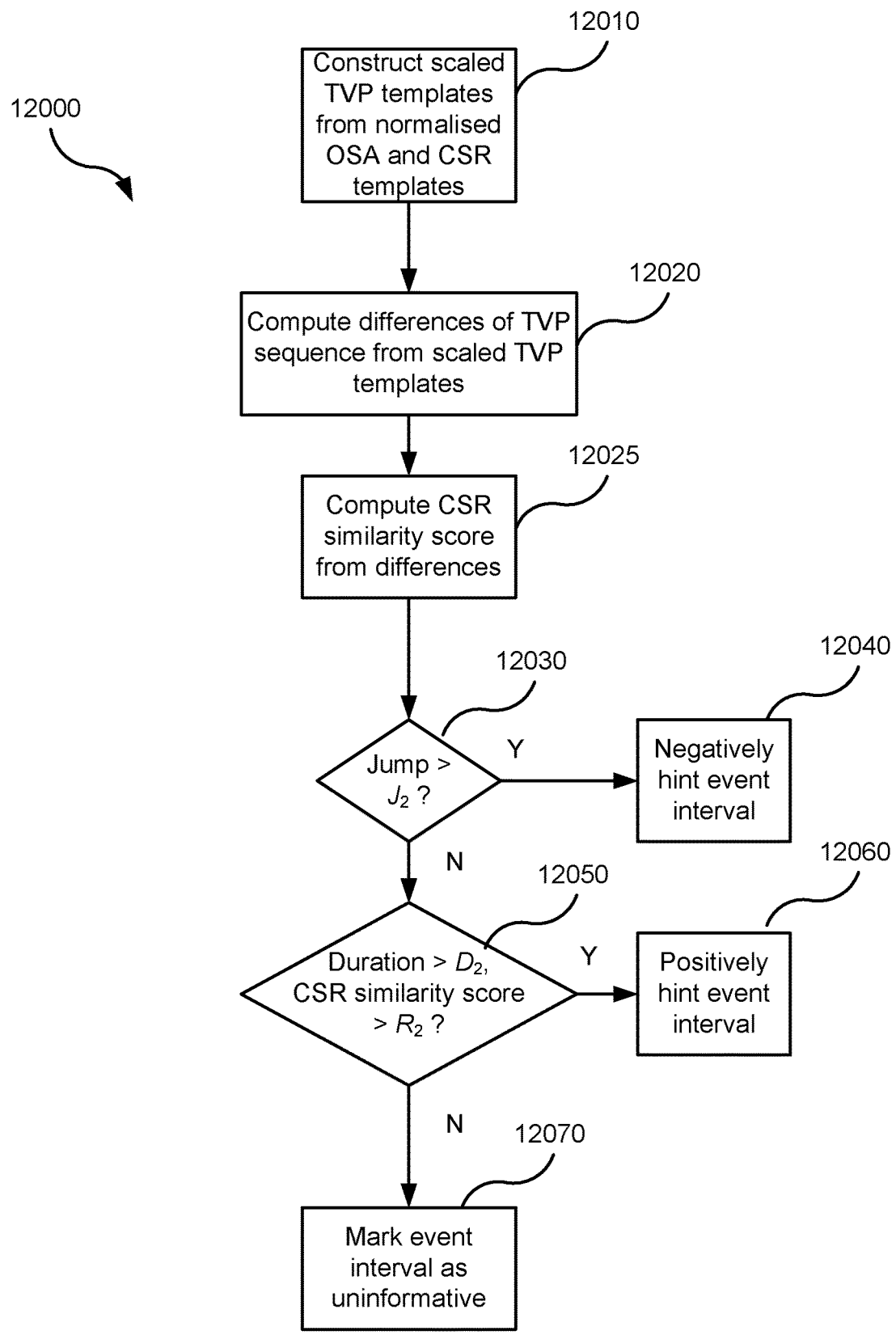

FIG. 12 contains a flow chart illustrating a method that may be used to implement the character determination step of the method of FIG. 10 in the case where the event interval was closed by an apnea event, in one form of the present technology.

Figure 13:
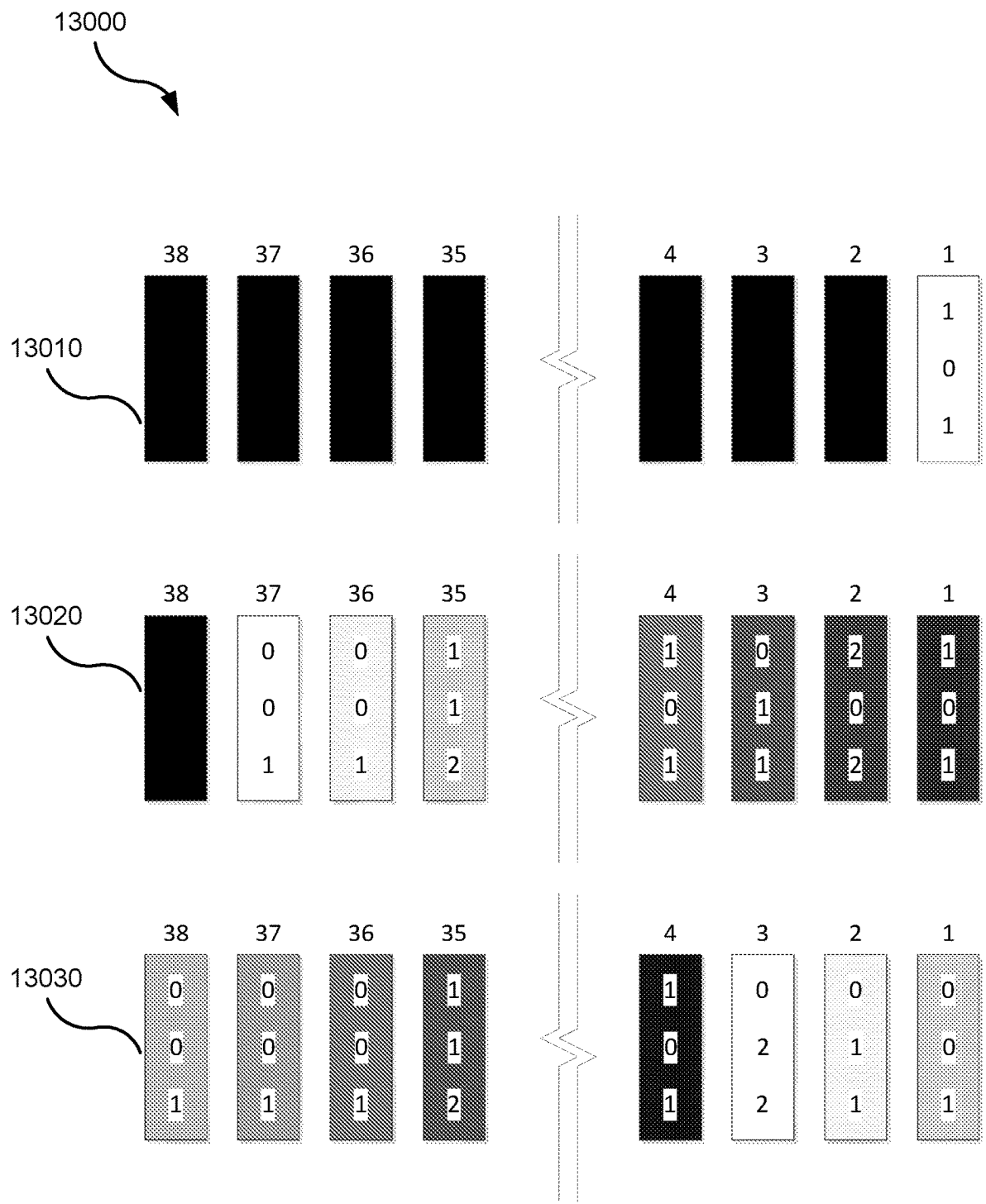

FIG. 13 illustrates an example of the evolution of the contents of the ring buffer recording the event interval statistics in an implementation with 38 bins in the ring buffer.

Figure 14:
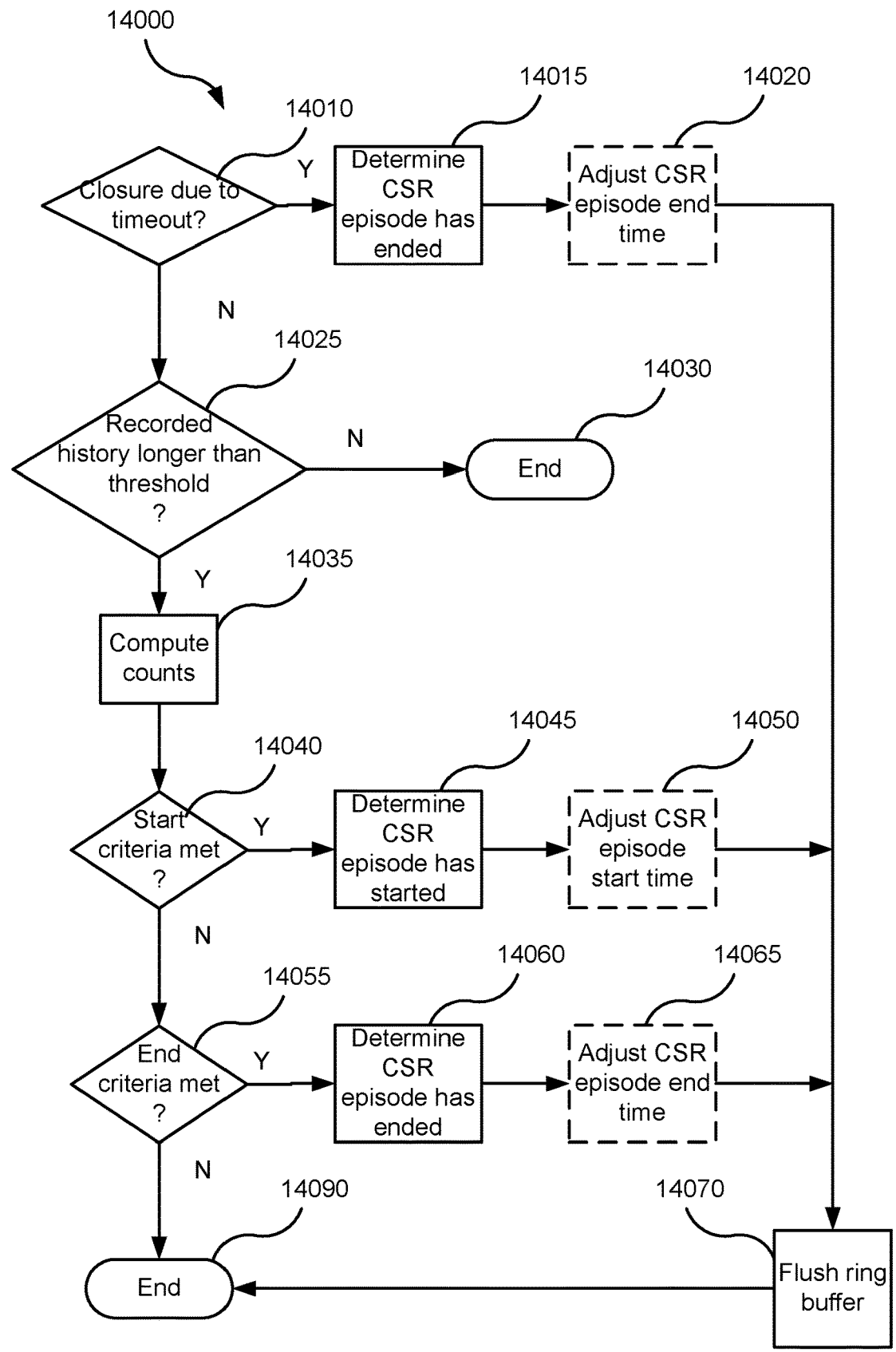

FIG. 14 contains a flow chart illustrating a method that may be used to implement the CSR state determination step of the method of FIG. 8 in one form of the present technology.

Figure 15A:
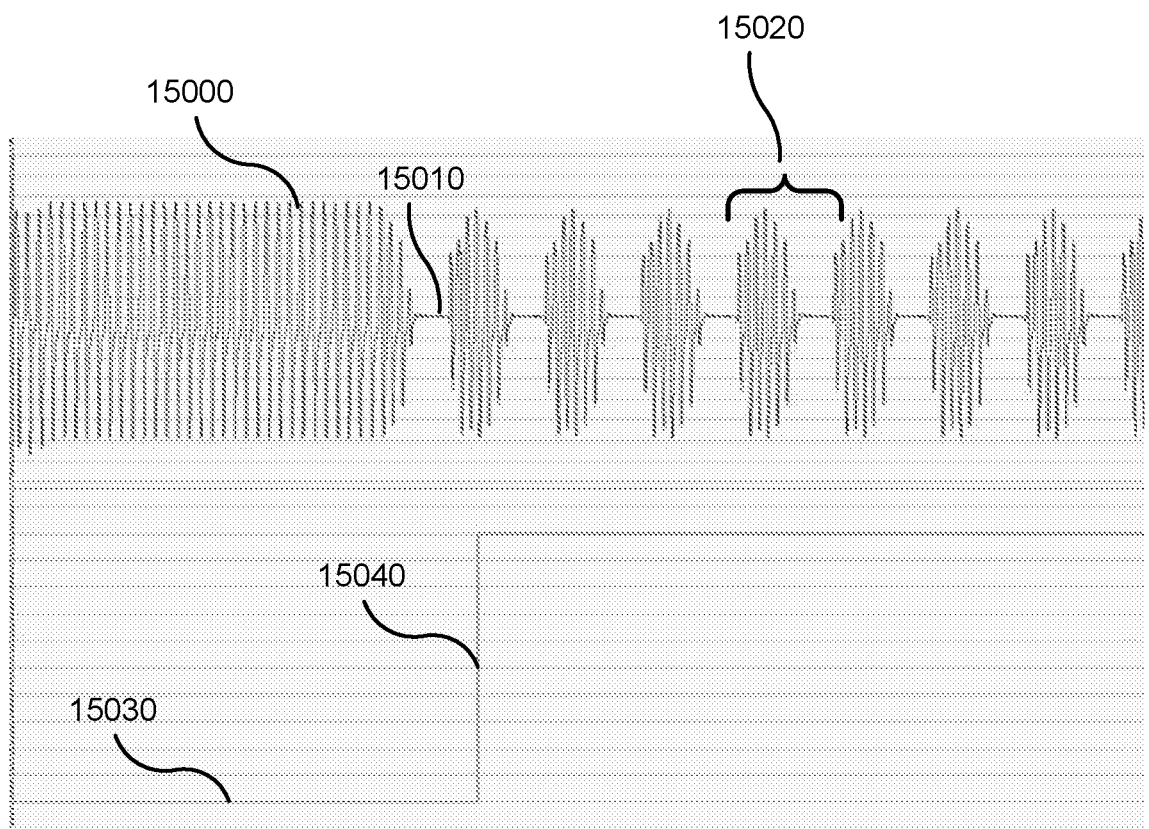

FIGS. 15Aa and 15B contain graphs illustrating the operation of the CSR detection algorithm of FIG. 4D on an example of respiratory flow.

Figure 15B:
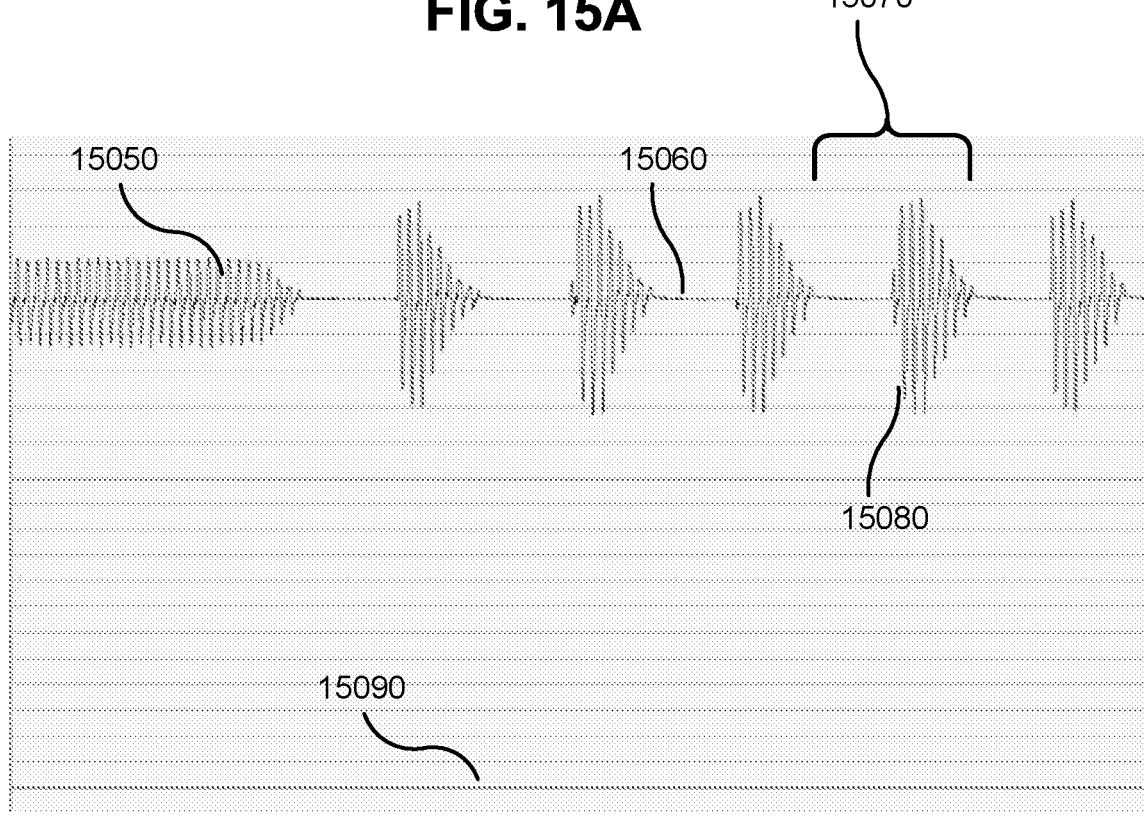
Figure 16:
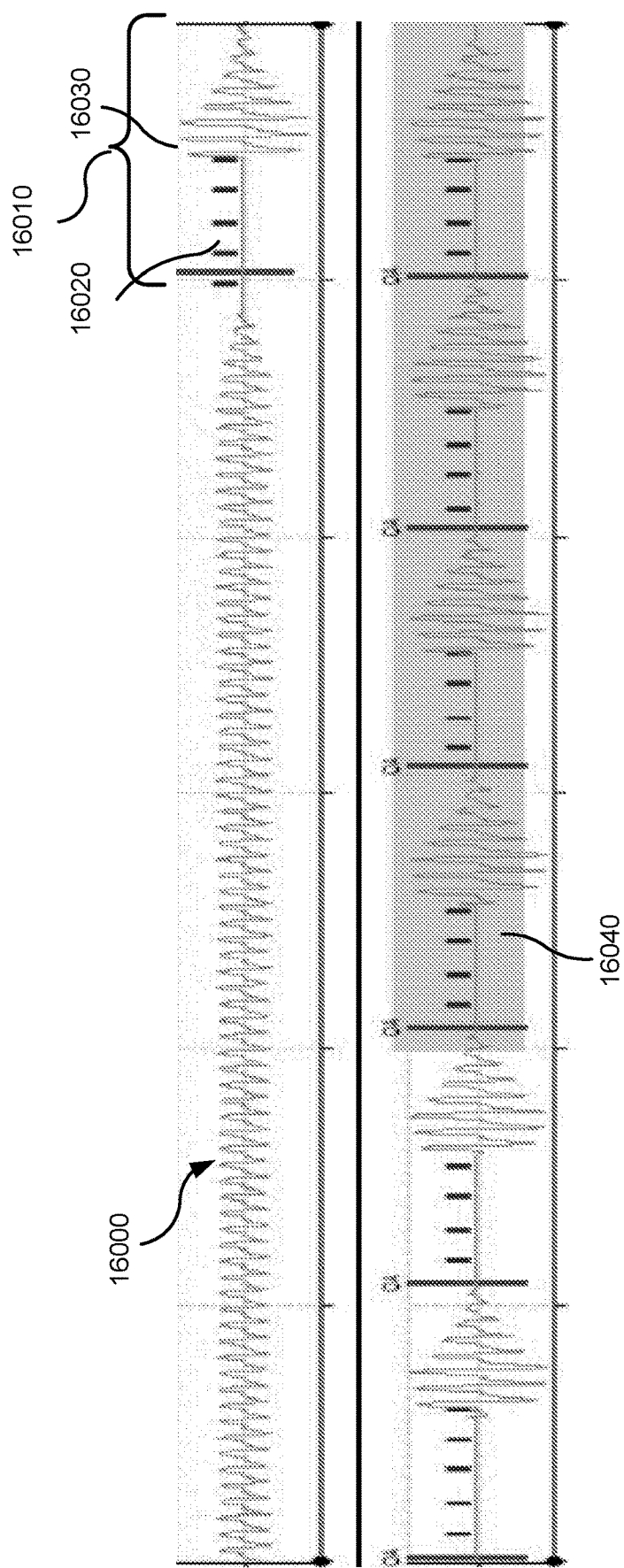

FIG. 16 contains a graph illustrating the operation of a previous CSR detection algorithm on the same example of respiratory flow as in FIG. 15B.

8 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

8.1 Therapy

In one form, the present technology comprises a method for treating a respiratory disorder comprising the step of applying positive pressure to the entrance of the airways of a patient 1000.

8.2 Treatment Systems

In one form, the present technology comprises apparatus for treating a respiratory disorder. The apparatus may comprise a PAP device 4000 for supplying pressurised respiratory gas, such as air, to the entrance of the airways of the patient 1000 via an air delivery tube leading to a patient interface 3000.

8.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

8.4 PAP Device

A preferred PAP device 4000 in accordance with one aspect of the present technology comprises mechanical and pneumatic components 4100 and electrical components 4200 and is programmed to execute one or more algorithms 4300. The PAP device 4000 preferably has an external housing 4010, preferably formed in two parts, an upper portion 4012 of the external housing 4010, and a lower portion 4014 of the external housing 4010. In alternative forms, the external housing 4010 may include one or more panel(s) 4015. Preferably the PAP device 4000 comprises a chassis 4016 that supports one or more internal components of the PAP device 4000. In one form a pneumatic block 4020 is supported by, or formed as part of the chassis 4016. The PAP device 4000 may include a handle 4018.

The pneumatic path of the PAP device 4000 preferably comprises an inlet air filter 4112, an inlet muffler 4122, a controllable pressure device 4140 capable of supplying air at positive pressure (preferably a blower 4142), and an outlet muffler 4124. One or more sensors or transducers 4270 are included in the pneumatic path.

The preferred pneumatic block 4020 comprises a portion of the pneumatic path that is located within the external housing 4010.

The PAP device 4000 preferably has an electrical power supply 4210, one or more input devices 4220, a processor 4230, a therapy device controller 4240, a therapy device 4245, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the PAP device 4000 may include more than one PCBA 4202.

8.4.1 PAP Device Mechanical & Pneumatic Components 4100

8.4.1.1 Air Filter(s) 4110

A PAP device in accordance with one form of the present technology may include an air filter 4110, or a plurality of air filters 4110.

In one form, an inlet air filter 4112 is located at the beginning of the pneumatic path upstream of a pressure device 4140.

In one form, an outlet air filter 4114, for example an antibacterial filter, is located between an outlet of the pneumatic block 4020 and a patient interface 3000.

8.4.1.2 Muffler(s) 4120

In one form of the present technology, an inlet muffler 4122 is located in the pneumatic path upstream of a pressure device 4140.

In one form of the present technology, an outlet muffler 4124 is located in the pneumatic path between the pressure device 4140 and a patient interface 3000.

8.4.1.3 Pressure Device 4140

In a preferred form of the present technology, a pressure device 4140 for producing a flow of air at positive pressure is a controllable blower 4142. For example the blower may include a brushless DC motor 4144 with one or more impellers housed in a volute. The blower may be preferably capable of delivering a supply of air, for example about 120 litres/minute, at a positive pressure in a range from about 4 cmH$_2$O to about 20 cmH$_2$O, or in other forms up to about 30 cmH$_2$O.

The pressure device 4140 is under the control of the therapy device controller 4240.

8.4.1.4 Transducer(s) 4270

In one form of the present technology, one or more transducers 4270 are located upstream of the pressure device 4140. The one or more transducers 4270 are constructed and arranged to measure properties of the air at that point in the pneumatic path.

In one form of the present technology, one or more transducers 4270 are located downstream of the pressure device 4140, and upstream of the air circuit 4170. The one or more transducers 4270 are constructed and arranged to measure properties of the air at that point in the pneumatic path.

In one form of the present technology, one or more transducers 4270 are located proximate to the patient interface 3000.

8.4.1.5 Anti-Spill Back Valve 4160

In one form of the present technology, an anti-spill back valve is located between the humidifier 5000 and the pneumatic block 4020. The anti-spill back valve is constructed and arranged to reduce the risk that water will flow upstream from the humidifier 5000, for example to the motor 4144.

8.4.1.6 Air Circuit 4170

An air circuit 4170 in accordance with an aspect of the present technology is constructed and arranged to allow a flow of air or breathable gasses between the pneumatic block 4020 and the patient interface 3000.

8.4.1.7 Supplemental Oxygen 4180

In one form of the present technology, supplemental oxygen 4180 is delivered to a point in the pneumatic path.

In one form of the present technology, supplemental oxygen 4180 is delivered upstream of the pneumatic block 4020.

In one form of the present technology, supplemental oxygen 4180 is delivered to the air circuit 4170.

In one form of the present technology, supplemental oxygen 4180 is delivered to the patient interface 3000.

8.4.2 PAP Device Electrical Components 4200

8.4.2.1 Power Supply 4210

In one form of the present technology power supply 4210 is internal of the external housing 4010 of the PAP device 4000. In another form of the present technology, power supply 4210 is external of the external housing 4010 of the PAP device 4000.

In one form of the present technology power supply 4210 provides electrical power to the PAP device 4000 only. In another form of the present technology, power supply 4210 provides electrical power to both PAP device 4000 and humidifier 5000.

8.4.2.2 Input Devices 4220

In one form of the present technology, a PAP device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the processor 4230.

In one form the input device 4220 may be constructed and arranged to allow a person to select a value and/or a menu option.

8.4.2.3 Processor 4230

In one form of the present technology, the processor 4230 is a processor suitable to control a PAP device 4000 such as an x86 INTEL processor.

A processor 4230 suitable to control a PAP device 4000 in accordance with another form of the present technology includes a processor based on ARM Cortex-M processor from ARM Holdings. For example, an STM32 series microcontroller from ST MICROELECTRONICS may be used.

Another processor 4230 suitable to control a PAP device 4000 in accordance with a further alternative form of the present technology includes a member selected from the family ARMS-based 32-bit RISC CPUs. For example, an STR9 series microcontroller from ST MICROELECTRONICS may be used.

In certain alternative forms of the present technology, a 16-bit RISC CPU may be used as the processor 4230 for the PAP device 4000. For example a processor from the MSP430 family of microcontrollers, manufactured by TEXAS INSTRUMENTS, may be used.

The processor 4230 is configured to receive input signal(s) from one or more transducers 4270, and one or more input devices 4220.

The processor 4230 is configured to provide output signal(s) to one or more of an output device 4290, a therapy device controller 4240, a data communication interface 4280 and humidifier controller 5250.

In some forms of the present technology, the processor 4230, or multiple such processors, is configured to implement the one or more methodologies described herein such as the one or more algorithms 4300 expressed as computer programs stored in a non-transitory computer readable storage medium, such as memory 4260. In some cases, as previously discussed, such processor(s) may be integrated with a PAP device 4000. However, in some forms of the present technology the processor(s) may be implemented discretely from the flow generation components of the PAP device 4000, such as for purpose of performing any of the methodologies described herein without directly controlling delivery of a respiratory treatment. For example, such a processor may perform any of the methodologies described herein for purposes of determining control settings for a ventilator or other respiratory related events by analysis of stored data such as from any of the sensors described herein.

The processor 4230 of the PAP device 4000 is programmed to execute one or more algorithms 4300, preferably including a pre-processing module 4310, a therapy engine module 4320, a therapy control module 4330, a reporting module 4335, and a fault condition detection module 4340.

8.4.2.4 Clock 4232

Preferably PAP device 4000 includes a clock 4232 that is connected to processor 4230.

8.4.2.5 Therapy Device Controller 4240

In one form of the present technology, therapy device controller 4240 is a therapy control module 4330 that forms part of the algorithms 4300 executed by the processor 4230.

In another form of the present technology, therapy device controller 4240 is a dedicated motor control integrated circuit. For example, in one form a MC33035 brushless DC motor controller, manufactured by ONSEMI is used.

8.4.2.6 Protection Circuits 4250

Preferably a PAP device 4000 in accordance with the present technology comprises one or more protection circuits 4250.

One form of protection circuit 4250 in accordance with the present technology is an electrical protection circuit.

One form of protection circuit 4250 in accordance with the present technology is a temperature or pressure safety circuit.

8.4.2.7 Memory 4260

In accordance with one form of the present technology the PAP device 4000 includes memory 4260, preferably non-volatile memory. In some forms, memory 4260 may include battery powered static RAM. In some forms, memory 4260 may include volatile RAM.

Preferably memory 4260 is located on PCBA 4202. Memory 4260 may be in the form of EEPROM, or NAND flash.

Additionally or alternatively, PAP device 4000 includes a removable form of memory 4260, for example a memory card made in accordance with the Secure Digital (SD) standard.

In one form of the present technology, the memory 4260 acts as a non-transitory computer readable storage medium on which is stored computer program instructions encoding the one or more methodologies described herein, such as the one or more algorithms 4300. The processor 4230 is configured to execute such instructions stored on the non-transitory computer readable storage medium.

8.4.2.8 Transducers 4270

Transducers may be internal of the PAP device 4000, or external of the PAP device 4000. External transducers may be located for example on or form part of the air circuit 4170, e.g. at the patient interface 3000. External transducers may be in the form of non-contact sensors such as a Doppler radar movement sensor that transmit or transfer data to the PAP device 4000.

8.4.2.8.1 Flow Transducer 4274

A flow transducer 4274 in accordance with the present technology may be based on a differential pressure transducer, for example, an SDP600 Series differential pressure transducer from SENSIRION. The differential pressure transducer is in fluid communication with the pneumatic circuit, with one of each of the pressure transducers connected to respective first and second points in a flow restricting element.

In one example, a signal representing total flow Qt from the flow transducer 4274 is received by the processor 4230.

8.4.2.8.2 Pressure Transducer 4272

A pressure transducer 4272 in accordance with the present technology is located in fluid communication with the pneumatic path. An example of a suitable pressure transducer 4272 is a sensor from the Honeywell ASDX series. An alternative suitable pressure transducer is a sensor from the NPA Series from General Electric.

In use, a signal from the pressure transducer 4272 is received by the processor 4230. In one form, the signal from the pressure transducer 4272 is filtered prior to being received by the processor 4230.

8.4.2.8.3 Motor Speed Signal 4276

In one form of the present technology a motor speed signal 4276 is generated. A motor speed signal 4276 is preferably provided by therapy device controller 4240. Motor speed may, for example, be generated by a speed sensor, such as a Hall effect sensor.

8.4.2.9 Data Communication Interface 4280

In one preferred form of the present technology, a data communication interface 4280 is provided, and is connected to processor 4230. Data communication interface 4280 is preferably connectable to remote external communication network 4282. Data communication interface 4280 is preferably connectable to local external communication network 4284. Preferably remote external communication network 4282 is connectable to remote external device 4286. Preferably local external communication network 4284 is connectable to local external device 4288.

In one form, data communication interface 4280 is part of processor 4230. In another form, data communication interface 4280 is an integrated circuit that is separate from processor 4230.

In one form, remote external communication network 4282 is the Internet. The data communication interface 4280 may use wired communication (e.g. via Ethernet, or optical fibre) or a wireless protocol to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such remote external device 4286 may be accessible to an appropriately authorised person such as a clinician.

Preferably, local external device 4288 is a personal computer, mobile phone, tablet, or remote control.

8.4.2.10 Output Device 4290 Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

8.4.2.10.1 Display Driver 4292

A display driver 4292 receives as an input the characters, symbols, or images intended for display on the display 4294, and converts them to commands that cause the display 4294 to display those characters, symbols, or images.

8.4.2.10.2 Display 4294

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

8.4.3 PAP Device Algorithms 4300

8.4.3.1 Pre-Processing Module 4310

A pre-processing module 4310 in accordance with the present technology receives, as an input, raw data from a transducer, for example a flow or pressure transducer, and preferably performs one or more process steps to calculate one or more output values that will be used as an input to another module, for example a therapy engine module 4320.

In one form of the present technology, the output values include the interface or mask pressure Pm, the respiratory flow Qr, and the leak flow Ql.

In various forms of the present technology, the pre-processing module 4310 comprises one or more of the following algorithms: pressure compensation 4312, vent flow 4314, leak flow 4316, respiratory flow 4318, and breath framer 4319.

8.4.3.1.1 Pressure Compensation 4312

In one form of the present technology, a pressure compensation algorithm 4312 receives as an input a signal indicative of the pressure in the pneumatic path proximal to an outlet of the pneumatic block 4020. The pressure compensation algorithm 4312 estimates the pressure drop in the air circuit 4170 and provides as an output an estimated pressure, Pm, in the patient interface 3000.

8.4.3.1.2 Vent Flow 4314

In one form of the present technology, a vent flow estimation algorithm 4314 receives as an input an estimated pressure, Pm, in the patient interface 3000 and estimates a vent flow of air, Qv, from a vent 3400 in a patient interface 3000.

8.4.3.1.3 Leak Flow 4316

In one form of the present technology, a leak flow algorithm 4316 receives as an input a total flow, Qt, and a vent flow Qv, and provides as an output a leak flow Ql by calculating an average of Qt-Qv over a period sufficiently long to include several breathing cycles, e.g. about 10 seconds.

In one form, the leak flow algorithm 4316 receives as an input a total flow Qt, a vent flow Qv, and an estimated pressure, Pm, in the patient interface 3000, and provides as an output a leak flow Ql by calculating a leak conductance, and determining a leak flow Ql to be a function of leak conductance and pressure, Pm. Preferably leak conductance is calculated as the quotient of low pass filtered non-vent flow Qt-Qv, and low pass filtered square root of pressure Pm, where the low pass filter time constant has a value sufficiently long to include several breathing cycles, e.g. about 10 seconds.

8.4.3.1.4 Respiratory Flow 4318

In one form of the present technology, a respiratory flow algorithm 4318 receives as an input a total flow, Qt, a vent flow, Qv, and a leak flow, Ql, and estimates a respiratory flow of air, Qr, to the patient, by subtracting the vent flow Qv and the leak flow Ql from the total flow Qt.

8.4.3.1.5 Breath Framer 4319

In one form of the present technology, a breath framer 4319 receives as input a respiratory flow of air to a patient, Qr, and provides as an output a series of "half-breath markers" indicating the end of each half-breath, that is, the end of the inspiratory portion and the end of the expiratory portion of each breath.

The breath framer 4319 also provides a series of measures of the magnitude of each half-breath as it ends. In one form of the present technology, the breath framer 4319 computes each half-breath magnitude as a tidal volume, that is, the integral of the absolute value of respiratory flow rate Qr over the interval between each successive pair of half-breath markers. In other forms, the half-breath magnitude is a peak flow rate of the absolute value of respiratory flow rate Qr over that interval, mean flow rate thereof, inspiratory/expiratory time, respiratory rate, or some other measure of magnitude of the half-breath.

8.4.3.2 Therapy Engine Module 4320

In one form of the present technology, a therapy engine module 4320 receives as inputs one or more of a pressure, Pm, in a patient interface 3000, and a respiratory flow of air to a patient, Qr, and provides as an output one or more therapy parameters.

In one form of the present technology, a therapy parameter is a CPAP treatment pressure Pt.

In one form of the present technology, a therapy parameter is one or more of a level of pressure support, and a target ventilation.

8.4.3.2.1 Phase Determination 4321

In one form of the present technology, a phase determination algorithm 4321 receives as an input a signal indicative of respiratory flow, Qr, and provides as an output a phase of a breathing cycle of a patient 1000.

In one form, the phase output is a discrete variable with values of either inhalation or exhalation.

In one form, the phase output is a discrete variable with values of one of inhalation, mid-inspiratory pause, and exhalation.

In one form, the phase output is a continuous variable, for example varying from 0 to 1, or 0 to $2\pi$.

In one form, the phase output is determined to have a discrete value of inhalation when a respiratory flow Qr has a positive value that exceeds a positive threshold. In one form, a phase is determined to have a discrete value of exhalation when a respiratory flow Qr has a negative value that is more negative than a negative threshold.

8.4.3.2.2 Ventilation Determination 4323

In one form of the present technology, a ventilation determination algorithm 4323 receives an input a respiratory flow Qr, and determines a measure indicative of patient ventilation, Vent.

In one form, ventilation determination algorithm 4323 determines a current value of patient ventilation, Vent, as the half the low-pass filtered absolute value of respiratory flow, Qr.

8.4.3.2.3 Waveform Determination 4322

In one form of the present technology, a control module 4330 controls a therapy device 4245 to provide positive airway pressure according to a predetermined waveform of pressure as a function of phase. In one form, the waveform is maintained at an approximately constant level for all values of phase. In one form, the waveform is a square wave, having a higher value for some values of phase, and a lower level for other values of phase.

In one form of the present technology a waveform determination algorithm 4322 receives as an input a value indicative of current patient ventilation, Vent, and provides as an output a waveform of pressure as a function of phase.

8.4.3.2.4 Determination of Inspiratory Flow Limitation 4324

In one form of the present technology, a processor executes one or more algorithms 4324 for the detection of inspiratory flow limitation.

In one form the algorithm 4324 receives as an input a respiratory flow signal Qr and provides as an output a metric of the extent to which the inspiratory portion of the breath exhibits inspiratory flow limitation.

In one form of the present technology, the inspiratory portion of each breath is identified by a zero-crossing detector. A number of evenly spaced points (for example, sixty-five), representing points in time, are interpolated by an interpolator along the inspiratory flow-time curve for each breath. The curve described by the points is then scaled by a scaler to have unity length (duration/period) and unity area to remove the effects of changing respiratory rate and depth. The scaled breaths are then compared in a comparator with a pre-stored template representing a normal unobstructed breath, similar to the inspiratory portion of the breath shown in FIG. 6A. Breaths deviating by more than a specified threshold (typically 1 scaled unit) at any time during the inspiration from this template, such as those due to coughs, sighs, swallows and hiccups, as determined by a test element, are rejected. For non-rejected data, a moving average of the first such scaled point is calculated by processor 4230 for the preceding several inspiratory events. This is repeated over the same inspiratory events for the second such point, and so on. Thus, for example, sixty five scaled data points are generated by processor 4230, and represent a moving average of the preceding several inspiratory events, e.g. three events. The moving average of continuously updated values of the (e.g. sixty five) points are hereinafter called the "scaled flow", designated as Qs(t). Alternatively, a single inspiratory event can be utilised rather than a moving average.

From the scaled flow, two shape factors relating to the determination of partial obstruction may be calculated.

Shape factor 1 is the ratio of the mean of the middle (e.g. thirty-two) scaled flow points to the mean overall (e.g. sixty-five) scaled flow points. Where this ratio is in excess of unity, the breath will be taken to be normal. Where the ratio is unity or less, the breath will be taken to be obstructed. A ratio of about 1.17 is taken as a threshold between partially obstructed and unobstructed breathing, and equates to a degree of obstruction that would permit maintenance of adequate oxygenation in a typical user.

Shape factor 2 is calculated as the RMS deviation from unit scaled flow, taken over the middle (e.g. thirty two) points. An RMS deviation of about 0.2 units is taken to be normal. An RMS deviation of zero is taken to be a totally flow-limited breath. The closer the RMS deviation to zero, the breath will be taken to be more flow limited.

Shape factors 1 and 2 may be used as alternatives, or in combination. In other forms of the present technology, the number of sampled points, breaths and middle points may differ from those described above. Furthermore, the threshold values can other than those described.

8.4.3.2.5 Determination of Apneas and Hypopneas 4325

In one form of the present technology, a processor 4230 executes one or more algorithms 4325 for the determination of the presence of apneas and/or hypopneas.

Preferably the one or more algorithms 4325 receive as an input a respiratory flow signal Qr and provide as an output an event that indicates the termination of an apnea or a hypopnea.

In one form, an apnea will be said to have been detected when a function of respiratory flow Qr falls below a flow threshold for a predetermined period of time. The function may determine a peak flow, a relatively short-term mean flow, or a flow intermediate of relatively short-term mean and peak flow, for example an RMS flow. The flow threshold may be a relatively long-term measure of flow.

In one form, a hypopnea will be said to have been detected when a function of respiratory flow Qr falls below a second flow threshold for a predetermined period of time. The function may determine a peak flow, a relatively short-term mean flow, or a flow intermediate of relatively short-term mean and peak flow, for example an RMS flow. The second flow threshold may be a relatively long-term measure of flow. The second flow threshold is greater than the flow threshold used to detect apneas.

8.4.3.2.6 Determination of Snore 4326

In one form of the present technology, a processor 4230 executes one or more snore algorithms 4326 for the detection of snore.

In one form the snore algorithm 4326 receives as an input a respiratory flow signal Qr and provides as an output a metric of the extent to which snoring is present.

Preferably the algorithm 4326 comprises the step of determining the intensity of the flow signal in the range of 30-300 Hz. Further preferably, algorithm 4326 comprises a step of filtering the respiratory flow signal Qr to reduce background noise, e.g. the sound of airflow in the system from the blower.

8.4.3.2.7 Determination of Airway Patency 4327

In one form of the present technology, a processor 4230 executes one or more algorithms 4327 for the determination of airway patency.

In one form, airway patency algorithm 4327 receives as an input a respiratory flow signal Qr, and determines the power of the signal in the frequency range of about 0.75 Hz and about 3 Hz. The presence of a peak in this frequency range is taken to indicate an open airway. The absence of a peak is taken to be an indication of a closed airway.

In one form, the frequency range within which the peak is sought is the frequency of a small forced oscillation in the treatment pressure Pt. In one implementation, the forced oscillation is of frequency 2 Hz with amplitude about 1 cmH$_2$O.

In one form, airway patency algorithm 4327 receives as an input a respiratory flow signal Qr, and determines the presence or absence of a cardiogenic signal. The absence of a cardiogenic signal is taken to be an indication of a closed airway.

8.4.3.2.8 Determination of Therapy Parameters 4328

In one form of the present technology, processor 4230 executes one or more algorithms 4328 for the determination of a therapy parameter, such as a target treatment pressure Pt. In one implementation, the therapy parameter determination algorithm 4328 receives as an input one of more of the following:
  i. A measure Π(t) (could be discrete, could be continuous) of respiratory phase at the current time t;
  ii. A waveform function Φ(Π) (could be a square wave, could be other waves) as a function of phase;
  iii. A measure of ventilation Vent;
  iv. A measure of inspiratory flow limitation;
  v. A measure of the presence of apnea and/or hypopnea;
  vi. A measure of the presence of snore; and
  vii. A measure of the patency of the airway.

In one form of the present technology, the therapy parameter determination algorithm 4328 computes an Amplitude A according to an integral control equation $$A = G\int(\text{Vent} - \text{Vtgt})dt \qquad (1)$$

where Vtgt is a target ventilation. In other forms, other modes of control could be used to compute the amplitude A, e.g. Proportional, Proportional Differential, Proportional Integral Differential.

The therapy parameter determination algorithm 4328 then computes the therapy parameter (the treatment pressure Pt) as $$Pt(t) = A*\Phi(\Pi(t)) + P_0 \qquad (2)$$

where $P_0$ is a "DC" component of pressure that may be a constant or may be a function of indices or measures of one or more of flow limitation, apnea, hypopnea, patency, and snore. (Note: In CPAP or APAP therapy A may be zero, in which case the treatment pressure equation (2) simplifies to $Pt = P_0$.)

In another form of the present technology, the algorithm 4328 determines the treatment pressure Pt as a function of indices or measures of one or more of flow limitation, apnea, hypopnea, patency, and snore. In one implementation, these measures are determined on a single breath basis, rather than on an aggregation of several previous breaths.

Figure 4E:
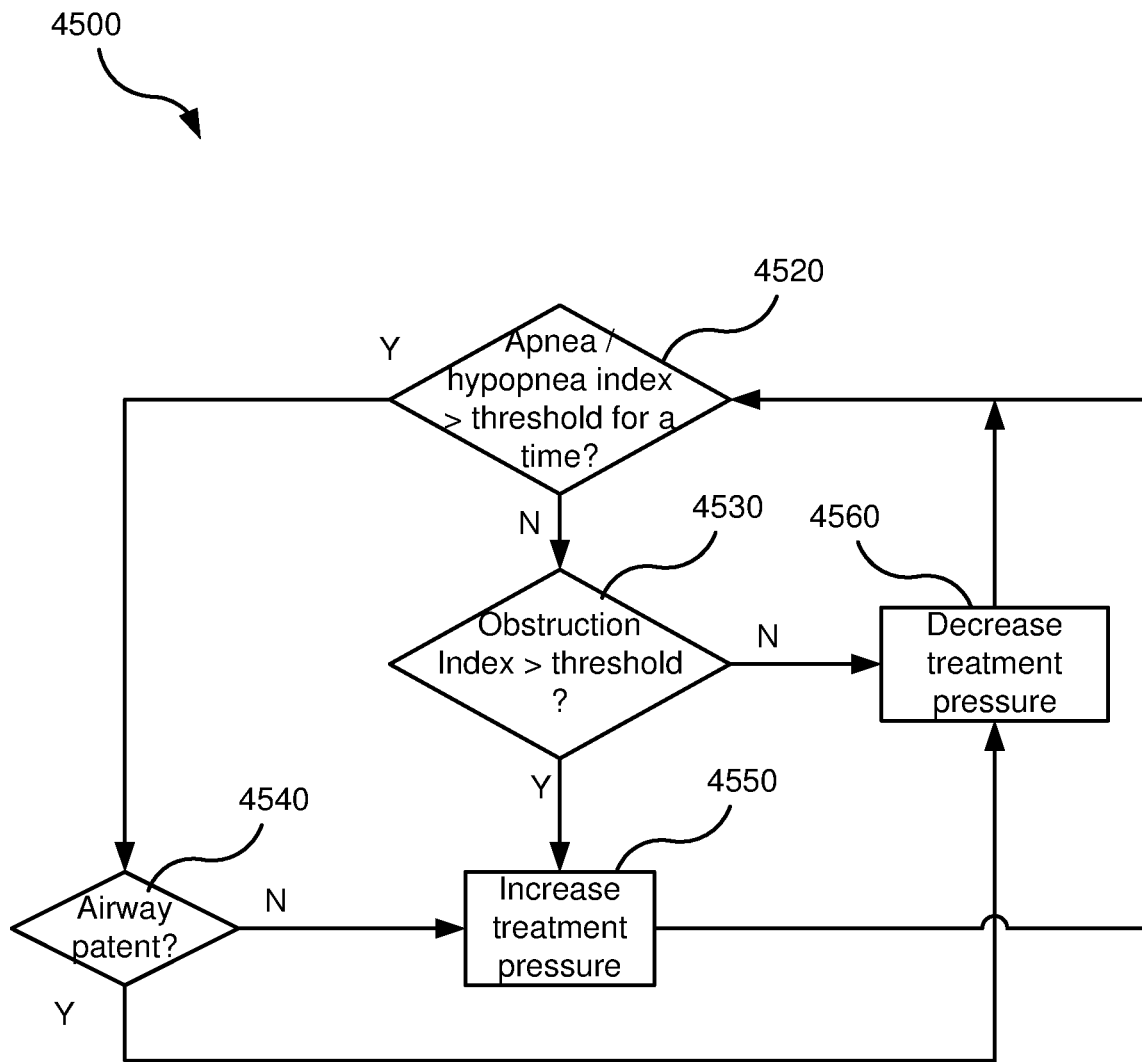
FIG. 4E is a flow chart illustrating a method 4500 carried out by the therapy engine module 4320 of FIG. 4D in accordance with one aspect of the present technology.

FIG. 4e is a flow chart illustrating a method 4500 carried out by the processor 4230 as one implementation of the algorithm 4328 in this form of the present technology. The method 4500 starts at step 4520, at which the processor 4230 compares the measure of the presence of apnea/hypopnea with a first threshold, and determines whether the measure of the presence of apnea/hypopnea has exceeded the first threshold for a predetermined period of time, indicating an apnea/hypopnea is occurring. If so, the method 4500 proceeds to step 4540; otherwise, the method 4500 proceeds to step 4530. At step 4540, the processor 4230 compares the measure of airway patency with a second threshold. If the measure of airway patency exceeds the second threshold, indicating the airway is patent, the detected apnea/hypopnea is deemed central, and the method 4500 proceeds to step 4560; otherwise, the apnea/hypopnea is deemed obstructive, and the method 4500 proceeds to step 4550.

At step 4530, the processor 4230 compares the measure of flow limitation with a third threshold. If the measure of flow limitation exceeds the third threshold, indicating inspiratory flow is limited, the method 4500 proceeds to step 4550; otherwise, the method 4500 proceeds to step 4560.

At step 4550, the processor 4230 increases the treatment pressure Pt by a predetermined pressure increment ΔP, provided the increased treatment pressure Pt would not exceed an upper limit P max. In one implementation, the predetermined pressure increment ΔP and upper limit P max are 1 cmH$_2$O and 20 cmH$_2$O respectively. The method 4500 then returns to step 4520.

At step 4560, the processor 4230 decreases the treatment pressure Pt by a decrement, provided the decreased treatment pressure Pt would not fall below a lower limit P min. The method 4500 then returns to step 4520. In one implementation, the decrement is proportional to the value of Pt−P min, so that the decrease in Pt to the lower limit P min in the absence of any detected events is exponential. Alternatively, the decrement in Pt could be predetermined, so the decrease in Pt to the lower limit P min in the absence of any detected events is linear.

8.4.3.2.9 Detection of Cheyne-Stokes Respiration 4329

In one form of the present technology, one or more processors may implement one or more of the methodologies described herein for detection of Cheyne Stokes respiration (CSR). For example, a processor 4230 may execute an algorithm 4329 to detect Cheyne-Stokes respiration (CSR). The one or more processors may for example be implemented in a PAP device that can provide a respiratory treatment, in a computer that analyses previously-recorded flow data input to the computer, or a monitor/detection device, such as an invasive or non-invasive device, having a sensor that measures and analyses signals indicative of patient flow, which may or may not provide a respiratory or other treatment.

In one form the algorithm 4329 receives as inputs the respiratory flow Qr, a series of apnea and/or hypopnea events provided by the apnea/hypopnea determination algorithm 4325, and a series of half-breath markers and corresponding half-breath magnitudes provided by the breath framer 4319. The CSR detection algorithm 4329 processes these inputs "on the fly" and returns parameters of each CSR episode as soon as, or soon after, they occur. In this respect the CSR detection algorithm 4329 may be said to operate in "real time". In one implementation, the CSR episode parameters are the start and end times of the CSR episode.

FIG. 6E shows data from a patient with Cheyne-Stokes respiration. Successive apnea events 6010, 6020, 6030, are marked.

FIG. 6F shows data from a patient with less severe Cheyne-Stokes respiration. Successive hypopnea events 6110, 6120, 6130, are marked.

A period bounded by successive apnea or hypopnea events is termed an "event interval." One such event interval 6040 bounded by two apnea events 6010, 6020 is illustrated in FIG. 6E. An event interval can also be closed after a predetermined period elapses without any apnea or hypopnea event (the "timeout condition"). Event intervals which the CSR detection algorithm 4329 determines to contain CSR are termed "CSR cycles". The primary work of the CSR detection algorithm 4329 is to determine which event intervals can be classified as CSR cycles, the other event intervals being classified as upper airway obstructions (as illustrated in FIG. 6D) and so unrelated to CSR. Once a sequence of consecutive event intervals have been determined to be CSR cycles, then the beginning of the first CSR cycle and the end of the last CSR cycle demark the beginning and end of a "CSR episode." The start time and end time of each CSR episode are returned by the CSR detection algorithm 4329.

FIG. 8 contains a flow chart illustrating a method 8000 that may be implemented by the CSR detection algorithm 4329 in one form of the present technology. The method 8000 starts at step 8010, which is an event handler that runs constantly to handle each apnea or hypopnea event that is provided by the apnea/hypopnea determination algorithm 4325. The event handler 8010 is described in detail below with reference to FIG. 9. The output of the event handler 8010 is a series of event intervals.

On receiving an event interval from the event handler 8010, step 8020 processes the event interval to determine its character: positively hinted (probably a CSR cycle), negatively hinted (probably not a CSR cycle), or uninformative. Step 8020 is described in more detail below with reference to FIGS. 10, 11, and 12. The next step 8030 updates event interval statistics based on the character determined in step 8020. Step 8030 is described in more detail below with reference to FIG. 13. Finally, step 8040 analyses the current event interval statistics to determine whether to change the CSR state. The CSR state, which may be a Boolean variable or other suitable data structure, indicates whether or not a CSR episode is currently taking place. Step 8040 is described in more detail below with reference to FIGS. 13 and 14.

Step 8040 applies a set of rules governing the interpretation of the current event interval statistics. Step 8040 considers a group of the most recent consecutive event intervals, such that if the balance of the group is positively hinted the group is taken as being part of a CSR episode, and if the balance is negatively hinted then the group is taken as not being part of a CSR episode. If the group is equally poised, then step 8040 makes no change to the current CSR state. The size of the group is defined by the number of event intervals that can accumulate in a history that is long compared to the typical length of a CSR cycle.

Previous approaches to detecting CSR analyse multiple recent candidate CSR cycles jointly, or in aggregate, to determine an overall CSR index score. This contrasts with the present approach of independently characterising successive event intervals and detecting CSR based on counts of recent event interval characteristics. The present approach may give fewer false detections of CSR because it is less likely to be dominated by a single event interval that, by chance, is particularly CSR-like or un-CSR-like. This advantage is accentuated by the analysis of a longer history of recent event intervals than has been the case in previous approaches.

FIG. 9 is a diagram of a hierarchical state machine (HSM) 9000 that may be implemented by the event handler 8010 of the method 8000 of FIG. 8 in one form of the present technology. The HSM 9000 starts at state 9010, which awaits the "first" apnea or hypopnea event. This "first" event need not literally be the first event in a monitoring session; it may be the first event after the closing of the previous event interval due to the timeout condition. The "first" apnea or hypopnea event that arrives opens an event interval and transitions the HSM 9000 to state 9020. In general, each event that occurs subsequent to the "first" event closes the current event interval as well as opening a new one. Closed event intervals are passed to step 8020 of method 8000 for processing. An exception to the general rule is that an apnea event causes any subsequent hypopnea event detected within a first predetermined period of comparable length to a typical hypopnea to be ignored, with the aim of not "double-handling" a single "low flow" event. In one implementation of the HSM 9000, the first predetermined period is less than a minute, for example, about half a minute (e.g., 25 seconds long). That is, a hypopnea event that occurs within, for example, 25 seconds of an apnea event does not close the current event interval or open a new one. For this purpose, state 9010 resets an "apnea timer" if the "first" event is an apnea event.

According to the timeout condition, if a second, longer predetermined period has elapsed since the previous event was handled, then the current event interval is closed and the HSM 9000 returns to state 9010 to await a new "first" event. To implement the timeout condition, state 9010 resets a "long timer" once a "first" event arrives. In one implementation, the second predetermined period is longer than the first predetermined period, and may be on the order of minutes, for example, the second predetermined period may be 180 seconds or about three minutes.

State 9020, which handles subsequent events, itself comprises a state machine, with sub-states 9030 and 9040. However, if the long timer times out while in state 9020, i.e. the timeout condition occurs, the HSM 9000 closes the current event interval and returns to state 9010 to await a "first" event.

In sub-state 9030, which is the entry state if the first event was a hypopnea, a new/subsequent hypopnea event detection closes the current event interval, opens a new event interval, resets the long timer, and causes the state 9020 to remain in sub-state 9030. A new/subsequent apnea event detection in sub-state 9030 closes the current event interval, opens a new event interval, resets the long timer and the apnea timer, and causes the state 9020 to transition to sub-state 9040.

In sub-state 9040, which is the entry state if the first event was an apnea, a hypopnea event is ignored. An apnea event in sub-state 9040 closes the current event interval, opens a new event interval, resets the long timer and the apnea timer, and causes the state 9020 to remain in sub-state 9040. An apnea timer timeout in sub-state 9040 causes the state 9020 to return to sub-state 9030, where a hypopnea event may be handled.

Once an event interval is opened, subsequent occurrences of a half-breath marker signal, signalling that a half-breath has been completed, and the magnitude of the half-breath are computed by the breath framer 4319 for the CSR detection algorithm 4329. When the breath framer 4319 signals each half-breath as completed and returns its magnitude, the CSR detection algorithm 4329 computes a measure of breathwise ventilation and records the measure in a sequential buffer associated with the current open event interval. In one implementation, the breathwise ventilation measure is the product of the current half-breath magnitude with the magnitude of the previous half-breath. In other implementations, measures of breathwise ventilation may be the sum of the current half-breath magnitude and the magnitude of the previous half-breath, the current half-breath magnitude itself, the arithmetic or geometric mean of the previous two or more half-breath magnitudes, or some other low-pass filtering of the recent half-breath magnitudes. In what follows, the tidal volume is used as the half-breath magnitude, and the tidal volume product ("TVP") which may be, for example, measured in square litres, is used as the measure of breathwise ventilation. Nevertheless, the described methods may implement other measures of half-breath magnitude and of breathwise ventilation.

There are exceptions to this general pattern of taking the product of the current half-breath tidal volume and the previous half-breath tidal volume for the breathwise ventilation. The first exception is when a "first" hypopnea event occurs that transitions the HSM 9000 from the waiting state 9010 to the handling state 9020. The CSR detection algorithm 4329 may not record the precursor half-breath tidal volumes, and so the tidal volume of the first half-breath that takes place after the "first" hypopnea may be ignored. The second exception is that the first half-breath after any apnea may also be ignored, since the tidal volume that is presented refers to the breath before the apnea, and so is irrelevant. Hypopnea events after the "first" event are not treated in an exceptional manner, in the sense that the tidal volume available from the first half-breath is multiplied by the prior value and stored in the sequential buffer. The reason is that the hypopnea event is quite delayed relative to the nadir of the tidal volumes, and so the recorded value is probably associated with the newly opened event interval.

In one implementation, the sequential buffer associated with the current open event interval may have a limited space, (e.g., only data space for 125 half-breath tidal volume products (TVPs)). Typically, in the majority of genuine CSR episodes there will not be more half-breaths in an event interval than this limit. Once an event interval is closed, the contents of the sequential buffer are forwarded to the step 8020 as a sequence of TVPs associated with the event interval, and the sequential buffer begins to be overwritten by TVPs associated with the newly opened event interval (if any).

FIG. 10 contains a flow chart illustrating a method 10000 that may be used to implement the event interval-processing step 8020 of the method 8000 of FIG. 8 in one form of the present technology.

The method 10000 begins at step 10010, which checks whether the event interval was closed by the timeout condition. If so ("Y"), step 10020 marks the event interval such that subsequent processing at step 8040 terminates the current CSR episode, if one is in progress, and the method 10000 concludes. Otherwise ("N"), the method 10000 proceeds to step 10030 to examine (a) the number of non-zero TVPs in the TVP sequence associated with the event interval and (b) the duration of the interval. For example, if there are fewer than a minimum number of non-zero TVPs, or the event interval duration is outside the duration range of a typical CSR cycle ("Y"), then at step 10040 the event interval is characterised as negatively hinted, and the method 10000 concludes. In one implementation, the duration range is from about 30 to 125 seconds, and the minimum number of non-zero TVPs is three. Otherwise ("N"), the minimum and maximum values TVP min and TVP max of the TVPs in the sequence are found and recorded at step 10050.

Step 10060 then calculates a value called the "relative maximum step" (considered a "jump" or sudden rise) feature. The relative maximum step feature is calculated as the maximum of the differences between successive TVPs in the sequence, normalised by TVP max. The first difference is simply set to the first TVP in the sequence. The significance of the relative maximum step feature is that the presence of a relatively sudden and large rise in a TVP sequence of an event interval suggests that the event interval is of an obstructive nature rather than due to CSR.

The step 10070 determines the character of the event interval (positively hinted, negatively hinted, or uninformative). The nature of the processing at step 10070 depends on whether the event interval was closed by an apnea event or a hypopnea event, i.e. on its "closure event". Step 10070 is described below in more detail with reference to FIGS. 11 and 12. The method 10000 then concludes.

FIG. 11 contains a flow chart illustrating a method 11000 that may be implemented as the event interval characterisation step 10070 in the case where the event interval was closed by a hypopnea event, in one form of the present technology. The method 11000 starts at step 11010, which constructs a scaled TVP template from a normalised template representing the expected sequence of TVP values consistent with the event interval being a lead-up to a CSR hypopnea (see FIG. 6F). The normalised template is defined so as to range between 0 and 1 on the domain [0, 1]. The number of values in the normalised template is set equal to the number of TVPs in the TVP sequence. The zero value of the normalised template occurs somewhat before the end of the domain, so that it coincides with the actual location of the hypopnea that ends the event interval, which is somewhat before the hypopnea event, due to the lag in the hypopnea detection portion of the algorithm 4325.

In one implementation of step 11010, the normalised template is constructed using the functional form $$y(x) = 1.4658\sin(\pi x)\cos(\pi x)\cos\left(\frac{\pi}{2}x\right) + 0.3195 \qquad (3)$$

Step 11010 constructs the scaled TVP template by scaling the normalised template y(x) to the range [TVP min, TVP max] as follows:

$$\text{ScaledTemplate}(x) = y(x)(\text{TVP max} - \text{TVP min}) + \text{TVP min} \qquad (4)$$

Step 11020 then computes a difference between the TVP sequence and the scaled TVP template. A low difference value indicates that the event interval has the character of the lead-up to a CSR hypopnea. In one implementation, the difference is the root mean square (RMS) deviation of the TVP sequence from the scaled TVP template.

The remaining steps 11030 to 11070 of the method 11000 apply rules for evaluation of the jump feature value, the difference, and the duration of the event interval to determine its character. At step 11030, the jump feature value is compared with a threshold $J_1$. If the jump feature value is greater than the threshold $J_1$ ("Y"), the event interval is characterised as negatively hinted at step 11040. Otherwise ("N"), if both the event interval duration is greater than a threshold $D_1$ and the difference of the TVP sequence from the scaled TVP template is less than a threshold $R_1$ ("Y" at step 11050), the event interval is characterised as positively hinted at step 11060. Otherwise ("N"), the event interval is marked as uninformative at step 11070. In one implementation, the rule thresholds are $J_1=0.6$, $D_1=35$ seconds, and $R_1=0.2$ square litres.

FIG. 12 contains a flow chart illustrating a method 12000 that may be implemented as the event interval characterisation step 10070 in the case where the event interval was closed by an apnea event, in one form of the present technology. The method 12000 starts at step 12010, which constructs two scaled TVP templates from respective normalised templates, one representing the expected sequence of TVP values consistent with the event interval being a lead-up to an OSA event (see FIG. 6D), and the other representing the expected sequence of TVP values consistent with the event interval being a lead-up to a CSR apnea (see FIG. 6E). The normalised templates are defined so as to range between 0 and 1 on the domain [0, 1]. The number of values in each normalised template is set equal to the number of TVPs in the TVP sequence. In one implementation of step 12010, the normalised OSA template is constructed using the functional form $$y_{OSA}(x) = \frac{1}{2}(1 + \cos(\pi x)) \quad (5)$$

In one implementation of step 12010, the normalised CSR template is constructed as the product of the raised half-wave cosine function and the Log-Normal distribution parameterised by a mean of zero and scale parameter of one, normalised so that the peak of the normalised CSR template reaches a magnitude of one. That is, the normalised CSR template may be constructed using the functional form $$y_{CSR}(x) = 1.917 \text{LogNormal}[0, 1](x) \times \frac{1}{2}(1 + \cos(\pi x)) \quad (6)$$

Step 12010 constructs two scaled TVP templates (the scaled OSA template and the scaled CSR template) by scaling each normalised template y(x) to the range [TVP min, TVP max] according to equation (4).

Step 12020 then computes differences of the TVP sequence from the scaled OSA template and the scaled CSR template, producing two numbers which may be considered an "Unlike OSA score" and an "Unlike CSR score" respectively. The reason that they are called "Unlike" scores is that the smaller the score, the closer the recorded TVP values are to the associated template, and conversely, the larger the score, the less the recorded TVP values resemble the template. A difference value of zero is achieved only when the recorded TVPs match the corresponding template perfectly. In one implementation, the differences are computed as RMS deviations.

A combined normalised score termed the "CSR Similarity score" is computed at step 12025 from the Unlike OSA score and the Unlike CSR score. The CSR similarity score is minimum for recorded TVPs that match the scaled OSA template perfectly and maximum for recorded TVPs that match the scaled CSR template perfectly. In one implementation, step 12025 computes the CSR similarity score by taking the difference of the Unlike OSA score and the Unlike CSR score, and dividing the result by the larger of the two scores. The resulting CSR similarity score is in the range of negative one (for recorded TVPs that match the scaled OSA template perfectly) to positive one (for recorded TVPs that match the scaled CSR template perfectly).

The remaining steps 12030 to 12070 of the method 12000 apply rules for evaluation of the jump feature value, the CSR similarity score, and the duration of the event interval to determine its character. At step 12030, the jump feature value is compared with a threshold $J_2$. If the jump feature value is greater than the threshold $J_2$ ("Y"), the event interval is characterised as negatively hinted at step 12040. Otherwise ("N"), if both the event interval duration is greater than a threshold $D_2$ and the CSR similarity is greater than a threshold $R_2$ ("Y" at step 12050), the event interval is characterised as positively hinted at step 12060. Otherwise ("N"), the event interval is marked as uninformative at step 12070. In one implementation, the rule thresholds are $J_2=0.6$, $D_2=40$ seconds, and $R_2=-0.15$.

As mentioned previously, the determination at step 8040 about the current presence or otherwise of an episode of CSR may be further made by considering additional event intervals, such as all the event intervals that have been processed in a history that is long compared to the typical length of a CSR cycle. Event intervals older than the history duration are not considered by step 8040. In one implementation, this history may be on the order of minutes or hours, such as, for example a duration of 19 minutes. However, other such history durations may be chosen so as to provide a suitable historic evaluation.

Step 8040 determines whether to set or change the CSR state based on any one or more, such as all, of the total count of event intervals in the history, the number of event intervals in the history that are positively hinted, and the number of event intervals in the history that are negatively hinted. (Other criteria may be applied/evaluated as well, such as the whether the event interval was closed by the timeout condition, or by the end of therapy.)

Step 8040 makes use of event interval statistics that have been updated according to the most recently closed event interval at step 8030. Step 8030 may optionally be implemented so as to maintain the statistics in a ring buffer containing $N_b$ bins, each of which corresponds to one of a sequence of windows of equal duration into which the history is notionally partitioned. Each bin is configured to contain a record comprising counts from event intervals, such as three different types of counts, for the event intervals that have ended in the corresponding window. For example, the different types of counts may include one or more of the number of event intervals having positively hinted character, the number of event intervals having negatively hinted character, and the total number of event intervals of the corresponding window, which includes the uninformative event intervals and those closed by the timeout condition. For reasons described below, the duration of each window is the time resolution of the CSR detection algorithm 4329, so the window duration is chosen to be roughly comparable with the length of a CSR cycle. In one form, each window is of duration 30 seconds. The number $N_b$ of bins in the ring buffer is the length of the history divided by the window duration. In one implementation, where the history is of duration 19 minutes and each window is of duration 30 seconds, there are $N_b=38$ bins in the ring buffer (19 minutes/ 30 seconds). Although a ring buffer is described in the example, other data structures may be implemented in the statistical collection/evaluation of the counts for CSR state determination.

While the HSM 9000 is in the waiting state 9010, the index to the current bin stays at one. Once the HSM 9000 has entered the "Handling Subsequent Events" state 9020, step 8030 advances the index to the "current" bin by one (modulo $N_b$) after each successive window elapses, until the HSM 9000 returns to the waiting state 9010. Step 8030 increments the relevant counts in the current bin only (the total count in all cases, and then possibly the positive hint count, or the negative hint count), depending on the character of the event interval just closed and processed by step 8020.

FIG. 13 illustrates an example 13000 of the evolution of the contents of an example ring buffer in an implementation with $N_b=38$ bins in the ring buffer. The bins are numbered 1 to 38 from right to left. The current bin is white, with older bins represented by progressively darker fill. The numbers in the bins represent the counts in each bin; from top to bottom, the number of positive hints, the number of negative hints, and the total number of event intervals. Row 13010 depicts the condition of the ring buffer shortly after the closure of the first event interval, where all of the bins have all zero counts except the current one (numbered 1), which has a positive count of one as the event interval was determined by step 8020 to be positively hinted. Row 13020 depicts the condition of the ring buffer shortly before 19 minutes have elapsed. The current bin is now numbered 37, and all the illustrated bins have at least one event interval recorded therein. Row 13030 depicts the condition of the ring buffer after 20.5 minutes have elapsed. The current bin is numbered 3, and the counts previously stored in bins 1, 2, and 3 have been overwritten with new counts related to the most recently closed event intervals.

Step 8040 analyses the event interval statistics after the processing of an event interval at step 8020 and the updating of the event interval statistics at step 8030.

FIG. 14 contains a flow chart illustrating a method 14000 that may be used to implement step 8040 in one form of the present technology.

The method 14000 starts at step 14010, which checks whether the event interval was closed due to the timeout condition (as marked at step 10020). If so ("Y"), step 14015 determines that the current CSR episode (if one is in progress) has ended, and sets the CSR state to False. The end time of the just-ended CSR episode is the current time. An optional step 14020 then adjusts the end time of the just-ended CSR episode in the manner described below. Any counts that may exist in the ring buffer are flushed at the next step 14070, and the method 14000 concludes at step 14090.

Otherwise ("N" at step 14010), step 14025 checks whether the statistical history recorded in the ring buffer is longer than a threshold that is somewhat less than the maximum possible length of the history. This step involves checking the age of the oldest bin in the history with a non-zero total event interval count. In one implementation in which the history is of duration 19 minutes, this threshold is 15 minutes. If not ("N"), the method 14000 concludes at step 14030, as there is insufficient information to alter the CSR state.

Otherwise ("Y" at step 14025), the method 14000 proceeds to step 14035, which computes three counts from the statistics recorded in the ring buffer:

$C^+$=the number of positively hinted event intervals in the history
$C^-$=the number of negatively hinted event intervals in the history
$C^T$=the total number of event intervals in the history Step 14040 then determines whether the three counts meet criteria indicating a CSR episode has started. The "start" criteria ensure that there have been sufficient event intervals in the history to form a reliable judgement, and the number of positively hinted event intervals is both comparable to the total number of event intervals and large compared to the number of negatively hinted event intervals. In one implementation, the three start criteria are as follows:

$$C^T \geq \left\lfloor \frac{H}{2} \right\rfloor$$

$$\frac{C^+}{C^T} \geq \frac{1}{2}$$

$$\frac{C^+}{C^-} \geq \frac{3}{2}$$

where $\lfloor \ \rfloor$ is the floor operator and H is the length of the history (in minutes). If the start criteria are all met ("Y" at step 14040), step 14045 determines that a CSR episode has started, and sets the CSR state to True. The start time of the just-started CSR episode is the current time. An optional step 14050 then adjusts the start time of the CSR episode in the manner described below. The method 14000 then proceeds to step 14070 to flush the ring buffer as described above.

If the start criteria are not met ("N" at step 14040), step 14055 determines whether the three counts meet criteria indicating a CSR episode has ended. The end criteria ensure that there have been sufficient event intervals in the history to form a reliable judgement, and the number of negatively hinted event intervals is comparable to the total number of event intervals. In one implementation, the two "end" criteria are as follows:

$$C^T \geq \left\lfloor \frac{H}{2} \right\rfloor - 2$$

$$\frac{C^-}{C^T} \geq \frac{1}{2}$$

If the end criteria are all met ("Y" at step 14055), step 14060 determines that the current CSR episode has ended, and sets the CSR state to False. The end time of the just-ended CSR episode is the current time. An optional step 14065 then adjusts the end time of the just-ended CSR episode in the manner described below. The method 14000 then proceeds to step 14070 to flush the ring buffer as described above.

If the end criteria are not met ("N" at step 14055), the method 14000 concludes at step 14090.

The adjustments of start or end time at optional steps 14020, 14050, and 14065 will now be described. As a consequence of the circumspection built into the CSR detection algorithm 4329, the instant that the start or end of a CSR episode is determined could be, and probably is, long after the CSR episode actually started or ended. Since the CSR detection algorithm 4329 returns the start and end times of each CSR episode, steps 14020, 14050, and 14065 perform some back-tracking to find the most appropriate times to return for those start and end times.

Once step 14015 determines that a CSR episode has ended due to the timeout condition, step 14020 adjusts the end time of the CSR episode by subtracting the duration of the "long timer" of the HSM 9000, equal to three minutes in one implementation.

Once step 14045 determines that a CSR episode has started, step 14050 adjusts the start time of the CSR episode by subtracting the duration of the CSR episode that has already elapsed. The elapsed duration of the CSR episode at the time that it is determined to have started is the age (to the beginning of the record) of the oldest record in the ring buffer that contains a non-zero positively hinted event interval count.

Once step 14060 determines that a CSR episode has ended due to the event interval statistics, step 14065 adjusts the end time of the CSR episode to be the time at the completion of the most recent record in the ring buffer that contains a non-zero positively hinted event interval count.

Since the resolution of the ages of the records in the history is the duration of a window corresponding to a bin, the elapsed duration also has a resolution equal to the duration of a window (30 seconds in the implementation mentioned above). Therefore the adjusted start and end times have a resolution equal to the window duration.

In a case of implementation in a PAP device, one additional situation may be addressed in the determination process. In some cases, a PAP device 4000 may be set by the user into a standby mode that indicates an "end of therapy" (for example, because a sales person was running a product demonstration). In this situation there are two possibilities depending on whether the most recent event interval that was not characterised as uninformative was positively or negatively hinted. If it was positively hinted, then the end time of the CSR episode is set to the time that the PAP device 4000 was set to standby mode. If it was negatively hinted, then the end time of the CSR episode is set to the beginning time of the negatively hinted event interval. Thus, the time may be set based on the mode of the PAP device (e.g., the standby mode).

In all cases, the elapsed duration is calculated from the (adjusted) start time to the (adjusted) end time to indicate the duration of the CSR episode.

The above-defined thresholds and templates are chosen specifically to distinguish CSR cycles from cycles of OSA events, which is why the algorithm 4329 is described as a "CSR detection" algorithm. However, the algorithm 4329 may be applied to distinguish other forms of periodic breathing that are punctuated by apneas or hypopneas, such as complex sleep apnea, from OSA cycles, by using other values of thresholds and templates. For this reason, the algorithm 4329 may be more generally described as a "periodic breathing detection" algorithm.

FIG. 15A contains a graph illustrating the operation of the CSR detection algorithm 4329. The top trace (trace 15000) represents respiratory flow Qt over approximately eight minutes of time. The lower trace 15030 represents the CSR state computed using the CSR detection algorithm 4329 based on the respiratory flow trace 15000. The respiratory flow trace 15000 commences with normal breathing, followed by a series of CSR cycles, e.g. 15020, each containing a complete apnea, e.g. 15010. The CSR state trace 15030 shows that the CSR state is not set to true by normal breathing, but rises to true at a time 15040 soon after the end of the apnea 15010 of the first CSR cycle, and remains true for the rest of the trace 15030 as the CSR episode continues.

FIG. 15B contains a graph further illustrating the operation of the CSR detection algorithm 4329. The top trace (trace 15050) represents respiratory flow Qt over approximately seven minutes. The lower trace 15090 represents the CSR state computed using the CSR detection algorithm 4329 based on the respiratory flow trace 15050. The respiratory flow trace 15050 commences with normal breathing, followed by a series of OSA cycles, e.g. 15070, each containing a complete obstructive apnea, e.g. 15060, followed by a rapid recovery, e.g. 15080. The CSR state trace 15090 shows that the CSR state is not set to true at any stage, either by the normal breathing or the OSA cycles in the respiratory flow trace 15050.

FIG. 16 contains a graph illustrating a false positive CSR identification in the operation of a CSR detection algorithm (EncorePro 2) running on a current market device (a Respironics REMStar Pro 2) on an identical flow signal to that used in FIG. 15B. In FIG. 16, the trace 16000 represents respiratory flow Qt over approximately twelve minutes. The respiratory flow trace 16000 shows a series of OSA cycles, e.g. 16010, each containing a complete obstructive apnea, e.g. 16020, followed by a rapid recovery, e.g. 16030. The grey shaded area 16040 indicates that the CSR detection algorithm incorrectly detects the presence of CSR, starting at about eight minutes and continuing to the end of the respiratory flow trace 16000.

8.4.3.3 Control Module 4330

In one form of the present technology, a control module 4330 in accordance with one aspect of the present technology receives as an input one or more therapy parameters, and controls a therapy device 4245 to deliver therapy in accordance with the therapy parameters.

In one form of the present technology, the therapy parameter is a target treatment pressure Pt.

In another form of the present technology, a control module 4330 in accordance with one aspect of the present technology receives as an input an EPAP pressure and an IPAP pressure, and controls a therapy device 4245 to deliver those respective pressures in synchronisation with the expiratory and inspiratory phases of the breathing cycle respectively.

In one form of the present technology, the control module 4330 responds to any CSR episode parameters provided by the CSR detection algorithm 4329 to adjust the therapy parameters provided by the therapy parameter determination algorithm 4328 so as to counteract the CSR.

8.4.3.4 Reporting Module 4335

The reporting module 4335 sends data from one or more of the modules in the pre-processing and therapy engine processing modules 4310 and 4320 to the data communication interface 4280. In one form of the present technology, the reporting module 4335 reports any CSR episode parameters provided by the CSR detection algorithm 4329 to the data communication interface 4280. The reported data may be saved in the memory 4260 of the PAP device 4000 and/or forwarded via the data communication interface 4280 to the local or remote external communication networks 4284 and 4282. In some forms of the present technology the processor 4230 may display details of the detected CSR episodes on the output device 4290.

8.4.3.5 Detection of Fault Conditions 4340

In one form of the present technology, the processor 4230 executes one or more methods for the detection of fault conditions. Preferably the fault conditions detected by the one or more methods includes at least one of the following:
  Power failure (no power, or insufficient power)
  Transducer fault detection
  Failure to detect the presence of a component
  Operating parameters outside recommended ranges (e.g. pressure, flow, temperature, $PaO_2$)
  Failure of a test alarm to generate a detectable alarm signal.

Upon detection of the fault condition, the corresponding algorithm signals the presence of the fault by one or more of the following:
  Initiation of an audible, visual &/or kinetic (e.g. vibrating) alarm
  Sending a message to an external device
  Logging of the incident

8.4.3.6 Therapy Device 4245

In a preferred form of the present technology, the therapy device 4245 is under the control of the control module 4330 to deliver therapy to a patient 1000.

Preferably the therapy device 4245 is a pressure device 4140 as described above.

8.5 Monitoring Systems

Another form of the present technology comprises apparatus for monitoring a patient 1000 with a respiratory disorder. The apparatus may comprise a monitoring device 7000 configured to monitor the respiratory movement of the patient 1000.

In one implementation, the monitoring device 7000 comprises components analogous to the following components of the PAP device 4000: processor 4230, clock 4232, power supply 4210, memory 4260, and data communication interface 4280.

The monitoring device 7000 also contains a non-contact sensor that generates a signal representing respiratory movement of the patient 1000. In one implementation, the non-contact sensor generates the respiratory movement signal by transmitting an RF pulse or series of pulses in the direction of the patient 1000 and analysing the reflections thereof from the chest of the patient 1000. The processor 4230 of the monitoring device 7000, typically a processor, is configured to perform the algorithms 4300 described above (with the exception of the therapy parameter determination algorithm 4328 and the control module 4330) using the respiratory movement signal provided by the non-contact sensor as a proxy for the respiratory airflow Qr.

In other forms of the present technology, apparatus for monitoring a patient 1000 with a respiratory disorder comprises a different monitoring device that makes use of a sensor that is configured to provide a respiratory movement signal according to a different modality, such as a chest band (plethysmograph).

In still other forms, the monitoring device may be an implantable device such as a CRT (cardiac resynchronization therapy) device and/or defibrillator such as one that measures respiratory movement or other signals indicative of respiration with one or more implanted electrodes.

8.6 Glossary

For the purposes of the present technology disclosure, in certain forms of the present technology, one or more of the following definitions may apply. In other forms of the present technology, alternative definitions may apply.

8.6.1 General

Air: In certain forms of the present technology, air supplied to a patient may be atmospheric air, and in other forms of the present technology atmospheric air may be supplemented with oxygen.

Continuous Positive Airway Pressure (CPAP): CPAP treatment will be taken to mean the application of a supply of air or breathable gas to the entrance to the airways at a pressure that is continuously positive with respect to atmosphere, and preferably approximately constant through a respiratory cycle of a patient. In some forms, the pressure at the entrance to the airways will vary by a few centimeters of water within a single respiratory cycle, for example being higher during inhalation and lower during exhalation. In some forms, the pressure at the entrance to the airways will be slightly higher during exhalation, and slightly lower during inhalation. In some forms, the pressure will vary between different respiratory cycles of the patient, for example being increased in response to detection of indications of partial upper airway obstruction, and decreased in the absence of indications of partial upper airway obstruction.

8.6.2 Aspects of PAP Devices

Air circuit: A conduit or tube constructed and arranged in use to deliver a supply of air or breathable gas between a PAP device and a patient interface. In particular, the air circuit may be in fluid connection with the outlet of the pneumatic block and the patient interface. The air circuit may be referred to as air delivery tube. In some cases there may be separate limbs of the circuit for inhalation and exhalation. In other cases a single limb is used.

APAP: Automatic Positive Airway Pressure. Positive airway pressure that is continually adjustable between minimum and maximum limits, depending on the presence or absence of indications of SDB events.

Blower or flow generator: A device that delivers a flow of air at a pressure above ambient pressure.

Controller: A device, or portion of a device that adjusts an output based on an input. For example one form of controller has a variable that is under control—the control variable—that constitutes the input to the device. The output of the device is a function of the current value of the control variable, and a set point for the variable.

Therapy: Therapy in the present context may be one or more of positive pressure therapy, oxygen therapy, carbon dioxide therapy, control of dead space, and the administration of a drug.

Positive Airway Pressure (PAP) device: A device for providing a supply of air at positive pressure to the airways.

Transducers: A device for converting one form of energy or signal into another. A transducer may be a sensor or detector for converting mechanical energy (such as movement) into an electrical signal. Examples of transducers include pressure sensors, flow sensors, carbon dioxide ($CO_2$) sensors, oxygen ($O_2$) sensors, effort sensors, movement sensors, noise sensors, a plethysmograph, and cameras.

8.6.3 Aspects of the Respiratory Cycle

Apnea: Preferably, apnea will be said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort.

Breathing rate: The rate of spontaneous respiration of a patient, usually measured in breaths per minute.

Duty cycle: The ratio of inhalation time, Ti to total breath time, Ttot.

Effort (breathing): Preferably breathing effort will be said to be the work done by a spontaneously breathing person attempting to breathe.

Expiratory portion of a breathing cycle: The period from the start of expiratory flow to the start of inspiratory flow.

Flow limitation: Preferably, flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Half-breath: The inspiratory or expiratory portion of a breathing cycle.

Hypopnea: Preferably, a hypopnea will be taken to be a reduction in flow, but not a cessation of flow. In one form, a hypopnea may be said to have occurred when there is a reduction in flow below a threshold for a duration. In one form in adults, the following either of the following may be regarded as being hypopneas:
  (i) a 30% reduction in patient breathing for at least 10 seconds plus an associated 4% desaturation; or
  (ii) a reduction in patient breathing (but less than 50%) for at least 10 seconds, with an associated desaturation of at least 3% or an arousal.

Inspiratory portion of a breathing cycle: Preferably the period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed.

Positive End-Expiratory Pressure (PEEP): The pressure above atmosphere in the lungs that exists at the end of expiration.

Peak flow (Qpeak): The maximum value of flow during the inspiratory portion of the respiratory flow waveform.

Respiratory flow, airflow, patient airflow, respiratory airflow (Qr): These synonymous terms may be understood to refer to the PAP device's estimate of respiratory airflow, as opposed to "true respiratory flow" or "true respiratory airflow", which is the actual respiratory flow experienced by the patient, usually expressed in litres per minute.

Tidal volume (Vt): The volume of air inhaled or exhaled during normal breathing, when extra effort is not applied.

(inhalation) Time (Ti): The duration of the inspiratory portion of the respiratory flow waveform.

(exhalation) Time (Te): The duration of the expiratory portion of the respiratory flow waveform.

(total) Time (Ttot): The total duration between the start of the inspiratory portion of one respiratory flow waveform and the start of the inspiratory portion of the following respiratory flow waveform.

Typical recent ventilation: The value of ventilation around which recent values over some predetermined timescale tend to cluster, that is, a measure of the central tendency of the recent values of ventilation.

Upper airway obstruction (UAO): includes both partial and total upper airway obstruction. This may be associated with a state of flow limitation, in which the level of flow increases only slightly or may even decrease as the pressure difference across the upper airway increases (Starling resistor behaviour).

Ventilation (Vent): A measure of the total amount of gas being exchanged by the patient's respiratory system, including both inspiratory and expiratory flow, per unit time. When expressed as a volume per minute, this quantity is often referred to as "minute ventilation". Minute ventilation is sometimes given simply as a volume, understood to be the volume per minute.

8.6.4 PAP Device Parameters

Flow rate: The instantaneous volume (or mass) of air delivered per unit time. While flow rate and ventilation have the same dimensions of volume or mass per unit time, flow rate is measured over a much shorter period of time. Flow may be nominally positive for the inspiratory portion of a breathing cycle of a patient, and hence negative for the expiratory portion of the breathing cycle of a patient. In some cases, a reference to flow rate will be a reference to a scalar quantity, namely a quantity having magnitude only. In other cases, a reference to flow rate will be a reference to a vector quantity, namely a quantity having both magnitude and direction. Flow will be given the symbol Q. Total flow, Qt, is the flow of air leaving the PAP device. Vent flow, Qv, is the flow of air leaving a vent to allow washout of exhaled gases. Leak flow, Ql, is the flow rate of unintentional leak from a patient interface system. Respiratory flow, Qr, is the flow of air that is received into the patient's respiratory system.

Leak: Preferably, the word leak will be taken to be a flow of air to the ambient. Leak may be intentional, for example to allow for the washout of exhaled $CO_2$. Leak may be unintentional, for example, as the result of an incomplete seal between a mask and a patient's face.

8.7 Other Remarks

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

8.8 Reference Label List patient 1000
bed partner 1100
patient interface 3000
seal-forming structure 3100
plenum chamber 3200
positioning and stabilising structure 3300
vent 3400
connection port 3600
forehead support 3700
PAP device 4000
external housing 4010
upper portion 4012
lower portion 4014
panel 4015
chassis 4016
handle 4018
pneumatic block 4020
pneumatic component 4100
air filter 4110
inlet air filter 4112
outlet air filter 4114
muffler 4120
inlet muffler 4122
outlet muffler 4124
pressure device 4140
blower 4142
motor 4144
back valve 4160
air circuit 4170
supplemental oxygen 4180
electrical component 4200
board Assembly PCBA 4202
power supply 4210
input device 4220
processor 4230
clock 4232
therapy device controller 4240
therapy device 4245
protection circuit 4250
memory 4260
transducer 4270
pressure transducer 4272
flow transducer 4274
motor speed signal 4276
data communication interface 4280
remote external communication network 4282
local external communication network 4284
remote external device 4286
local external device 4288
output device 4290
display driver 4292
display 4294
algorithms 4300
pre-processing module 4310
pressure compensation algorithm 4312
vent flow calculation algorithm 4314
leak flow calculation algorithm 4316
respiratory flow algorithm 4318
breath framer 4319
therapy engine module 4320
phase determination algorithm 4321
waveform determination algorithm 4322
form ventilation determination algorithm 4323
flow limitation determination algorithm 4324
apnea/hypopnea determination algorithm 4325
snore determination algorithm 4326
airway patency algorithm 4327
therapy parameter determination algorithm 4328
CSR detection algorithm 4329
control module 4330
reporting module 4335
fault condition detection module 4340
method 4500
humidifier 5000
humidifier controller 5250
apnea event 6010
apnea event 6020
apnea event 6030
event interval 6040
hypopnea event 6110
hypopnea event 6120
hypopnea event 6130
monitoring device 7000
method 8000
event handler 8010
HSM 9000
method 10000
method 11000
method 12000
example 13000
row 13010
row 13020
row 13030
method 14000
trace 15000
apnea 15010
CSR cycle 15020
trace 15030
time 15040
trace 15050
apnea 15060
OSA cycle 15070
recovery 15080
trace 15090
trace 16000
OSA cycle 16010
apnea 16020
recovery 16030
shaded area 16040

The invention claimed is:

1. A method in a processor for detecting periodic breathing by a patient, the method comprising:
   receiving in a processor a series of event intervals bounded by apnea or hypopnea events detected in respiration of the patient;
   processing in the processor, upon closure of an event interval, the event interval to determine a character of the event interval, wherein the processor determines the character of the event interval using a group of characterizations comprising:
      probably a periodic breathing cycle;
      probably not a periodic breathing cycle; and
      uninformative;
   determining in the processor whether to change a current periodic breathing state that indicates whether a periodic breathing episode is in progress, based on a history of the event interval characters determined using the group of characterizations, the history being greater than a typical length of a periodic breathing cycle; and
   generating an output indicating the current periodic breathing state.

2. The method according to claim 1, further comprising reporting a parameter of a detected periodic breathing episode.

3. The method according to claim 1, wherein the patient is undergoing therapy for a breathing disorder, further comprising adjusting one or more parameters of the therapy in response to a detected periodic breathing episode.

4. The method according to claim 1, wherein the processing is dependent on a sequence of measures of breathwise ventilation associated with the event interval.

5. The method according to claim 4, wherein each of the measures of breathwise ventilation is a product of a magnitude of a current half-breath and a magnitude of a previous half-breath.

6. The method according to claim 5, wherein the magnitude of a half-breath is a tidal volume of the half-breath.

7. The method according to claim 4, wherein the processing comprises determining that the event interval was probably not a periodic breathing cycle if a duration of the event interval is outside a range of a typical periodic breathing cycle, or the sequence of measures of breathwise ventilation contains fewer than a minimum number of non-zero measures of breathwise ventilation.

8. The method according to claim 4, wherein the processing further comprises computing a relative maximum step feature from the sequence of measures of breathwise ventilation.

9. The method according to claim 8, wherein the processing further comprises, in a case of the event interval being closed by a hypopnea event:
   constructing a template representing an expected sequence of breathwise ventilation measures consistent with the event interval being a lead-up to a periodic breathing hypopnea;
   computing a difference between the sequence of breathwise ventilation measures and the template; and
   determining the character of the event interval based on the relative maximum step feature and the difference.

10. The method according to claim 9, wherein the determining comprises:
    determining that the event interval was probably not a periodic breathing cycle if the relative maximum step feature exceeds a first threshold; and
    determining that the event interval was probably a periodic breathing cycle if the difference is less than a second threshold and a duration of the event interval is greater than a third threshold.

11. The method according to claim 8, wherein the processing further comprises, in a case of the event interval being closed by an apnea event:
    constructing a template representing an expected sequence of breathwise ventilation measures consistent with the event interval being a lead-up to an obstructive sleep apnea;
    constructing a template representing an expected sequence of breathwise ventilation measures consistent with the event interval being a lead-up to a periodic breathing apnea;
    computing differences between the sequence of breathwise ventilation measures and each template;
    computing a periodic breathing similarity score from the differences; and
    determining the character of the event interval based on the relative maximum step feature and the periodic breathing similarity score.

12. The method according to claim 11, wherein the determining comprises:
    determining that the event interval was probably not a periodic breathing cycle if the relative maximum step feature exceeds a first threshold; and
    determining that the event interval was probably a periodic breathing cycle if the periodic breathing similarity score is greater than a second threshold and a duration of the event interval is greater than a third threshold.

13. The method according to claim 1, wherein the determining comprises:
    computing a count of event intervals in the history of the event interval characters that were probably periodic breathing cycles, a count of event intervals in the history that were probably not periodic breathing cycles, and a total count of event intervals in the history;
    changing the current periodic breathing state to true if the counts meet start criteria; and
    changing the current periodic breathing state to false if the counts meet end criteria.

14. The method according to claim 13, further comprising, upon changing the periodic breathing state to true, adjusting a start time of a just-started periodic breathing episode.

15. The method according to claim 13, further comprising, upon changing the current periodic breathing state to false, adjusting an end time of a just-ended periodic breathing episode.

16. The method according to claim 1, wherein the determining comprises changing the current periodic breathing state to false if the event interval was closed by a timeout.

17. The method of claim 1 wherein the processor maintains a record comprising a count of event intervals for each of the characterizations of the group of characterizations.

18. The method of claim 1 wherein the processor determines that the character of the event interval is uninformative if the character of the event interval is determined not to be either (a) probably a periodic breathing cycle, or (b) probably not a periodic breathing cycle.

19. A device for detecting periodic breathing in a patient, the device comprising:
    a sensor configured to provide a signal representing respiratory airflow of the patient; and
    a processor configured to detect periodic breathing in a patient, wherein the processor is configured to:

receive a series of event intervals bounded by apnea or hypopnea events detected in respiration of the patient using the signal from the sensor;

process, upon closure of an event interval, the event interval to determine a character of the event interval, wherein the processor is configured to determine the character of an event interval using a group of characterizations comprising: (a) probably a periodic breathing cycle; (b) probably not a periodic breathing cycle; and (c) uninformative;

determine whether to change a current periodic breathing state that indicates whether a periodic breathing episode is in progress, based on a history of the event interval characters determined using the group of characterizations, the history being greater than a typical length of a periodic breathing cycle; and generate an output indicating the current periodic breathing state.

20. The device according to claim 19, further comprising a therapy device configured to provide therapy to the patient for a breathing disorder, wherein the processor is further configured to adjust one or more parameters of the therapy in response to a detected periodic breathing episode.

21. The device according to claim 19, further comprising a data communication interface coupled with the processor, wherein the processor is further configured to report a parameter of a detected periodic breathing episode through the data communication interface to an external device.

22. The device of claim 19 wherein the processor is further configured to maintain a record comprising a count of event intervals for each of the characterizations of the group of characterizations.

23. The device of claim 19 wherein the processor is configured to determine that the character of the event interval is uninformative if the character of the event interval is determined not to be (a) and not to be (b).

24. A non-transitory computer-readable storage medium on which are stored program code instructions configured to cause a processor to carry out a method of detecting periodic breathing in a patient, the method comprising:

receiving a series of event intervals bounded by apnea or hypopnea events detected in respiration of the patient;

processing, upon closure of an event interval, the event interval to determine a character of the event interval, wherein the processor determines the character of the event interval using a group of characterizations comprising: (a) probably a periodic breathing cycle; (b) probably not a periodic breathing cycle; and (c) uninformative;

determining whether to change a current periodic breathing state that indicates whether a periodic breathing episode is in progress, based on a history of the event interval characters determined using the group of characterizations, the history being greater than a typical length of a periodic breathing cycle; and generating an output indicating the current periodic breathing state.

25. The non-transitory computer-readable storage medium of claim 24 wherein the stored program code instructions are further configured to cause a processor to maintain a record comprising a count of event intervals for each of the characterizations of the group of characterizations.

26. The non-transitory computer-readable storage medium of claim 24 wherein the stored program code instructions are further configured to cause a processor to determine that the character of the event interval is uninformative if the event interval is determined not to be (a) and not to be (b).

27. A method in a processor for detecting periodic breathing by a patient, the method comprising:

receiving in a processor a series of event intervals bounded by apnea or hypopnea events detected in respiration of the patient;

processing in the processor, upon closure of an event interval, the event interval to determine a character of the event interval, wherein the character of an event interval is one of:
probably a periodic breathing cycle;
probably not a periodic breathing cycle; and
uninformative;

determining in the processor whether to change a current periodic breathing state that indicates whether a periodic breathing episode is in progress, based on a history of the event interval characters that is greater than a typical length of a periodic breathing cycle; and generating an output indicating the current periodic breathing state, wherein the processing is dependent on a sequence of measures of breathwise ventilation associated with the event interval, and wherein each of the measures of breathwise ventilation is a product of a magnitude of a current half-breath and a magnitude of a previous half-breath.

28. A device for detecting periodic breathing in a patient, the device comprising:

a sensor configured to provide a signal representing respiratory airflow of the patient; and a processor configured to detect periodic breathing in a patient, wherein the processor is configured to:

receive a series of event intervals bounded by apnea or hypopnea events detected in respiration of the patient using the signal from the sensor;

process, upon closure of an event interval, the event interval to determine a character of the event interval, wherein the character of an event interval is one of: probably a periodic breathing cycle; probably not a periodic breathing cycle; and uninformative;

determine whether to change a current periodic breathing state that indicates whether a periodic breathing episode is in progress, based on a history of the event interval characters that is greater than a typical length of a periodic breathing cycle; and generate an output indicating the current periodic breathing state, wherein the process to determine the character of the event interval is dependent on a sequence of measures of breathwise ventilation associated with the event interval, and wherein each of the measures of breathwise ventilation is a product of a magnitude of a current half-breath and a magnitude of a previous half-breath.

* * * * *